(12) United States Patent
Rosenberg et al.

(10) Patent No.: US 8,530,169 B2
(45) Date of Patent: *Sep. 10, 2013

(54) METHODS FOR DETERMINING OLIGOSACCHARIDE BINDING

(75) Inventors: Robert D. Rosenberg, Staten Island, NY (US); Zhengliang Wu, Edina, MN (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/835,554

(22) Filed: Jul. 13, 2010

(65) Prior Publication Data

US 2011/0064715 A1 Mar. 17, 2011

Related U.S. Application Data

(63) Continuation of application No. 10/263,338, filed on Oct. 1, 2002, now Pat. No. 7,754,432.

(60) Provisional application No. 60/326,270, filed on Oct. 1, 2001.

(51) Int. Cl.
*G01N 33/53* (2006.01)

(52) U.S. Cl.
USPC .......................................... 435/7.1; 436/518

(58) Field of Classification Search
None
See application file for complete search history.

(56) References Cited

U.S. PATENT DOCUMENTS

| | | | |
|---|---|---|---|
| 5,403,927 A | 4/1995 | Bendiak | |
| 5,449,781 A | 9/1995 | Varki et al. | |
| 5,468,620 A | 11/1995 | Molloy et al. | |
| 6,054,047 A | 4/2000 | Hindsgaul et al. | |
| 6,287,847 B1 | 9/2001 | Hefti | |

OTHER PUBLICATIONS

Galanina et al. (Tumor Biology 1998 vol. 19, p. 79-87).*
Atha et al. (Biochemistry 1985 vol. 24, p. 6723-6729).*
Jacob van den Born et al. J. Biol. Chem. 1995 vol. 270, p. 31303-31309).*
Fischer et al. (Biochem. J. 1996 vol. 318, p. 1051-1056).*
Andres et al. (1992) The Journal of Biological Chemistry, Binding of Two Growth Factor Families to Separate Domains of the Proteoglycan Betaglycan, 267:5927-5930, The American Society for Biochemistry and Molecular Biology, Inc.
Atha et al. (1985) Biochemistry, Contribution of Monosaccharide Residues in Heparin Binding to Antithrombin III, American Chemical Society 1995, 24:6723-6729.
Bellot at al. (1991) The Embo Journal, Ligand-Induced Transphosphorylation Between Different FGF Receopts, Oxford University Press. 10:2849-2854.
Bernfield et al. (1999) Functions of Cell Surface Heparan Sulfate Proteoglycans, Ann. Rev. Biochem. Annual Reviews. 68:729-777.
Carthew ey al. (1985) An RNA Polymerase II Transciption Factor Binds to an Upstram Element in the Adenovirus Major Late Promoter, 1985 MIT Cell vol. 43:439-448.
DiGabriele et al. (1998) Structure of a Heparin-Linked Biologically Active Dimer of Fibroblast Growth Factor, Macmillan Publishers Ltd 1998, Nature 393:812-817.
Faham et al.(1996) Heparin Structure and Interactions With Basic Fibroblat Growth Factor, Science 271:1116-11120.
Fried and Crothers (1981) Equilibria and Kinetics of LAC Repressor-Operator Interactions by Polyacrylamide Gel Electrophoresis, IRI Press Limited, Nuclear Acids Research vol. 9:6505-6525.
Gambarini, et al. (1993) Mitogenic Activity of Acidic Fibroblast Growth Factor Is Enhanced by Highly Sulfated Oligosaccharides Derived From Heparin and Heparan Sulfate, Molecular and Cellular Biochemistry, Kluwer Academic Publishers, vol. 124: 121-129.
Givol and Yayon (1992) Complexity of FGF Receptors: Genetic Basis for Structural Diversity and Functional Specificity, The FASEB Journal. 6:3362-2269.
Guimond et al. (1993) Activating and Inhibitory Heparin Sequences for FGF-2 (Basic FGF) The Journal of Biological Chemistry, The American Society for Biochemistry and Molecular Biology, Inc 268:23906-23914.
Heldin (1995) Dimerization of Cell Surface Receiptors in Signal Transduction, Cell Press, Cell vol. 80: 213-223.
Higashiyama et al (1993) Heparin-Binding EGF-Like Growth Factor Stimulation of Smooth Muscle Cell Migration: Dependence on Interactions With Cell Surface Heparan Sulfate, The Rockefeller University Press, The Journal of Cell Biology, vol. 122:933-940.
Hsu (1999) Heparin Is Essential for a Signle Keratinocyte Growth Factor Molecule to Bind and Form a Complex With Two Molecules of the Extracellular Domain of Its Receptor, American Chemical Society, Biochemistry 38:2523-2534.
Kariya, et al (2000), Preparation of Completely 6-0-Desulfated Heparin and Its Ability Fo Enhance Activity of Basic Fibroblast Growth Factor, The journal of Biological Chemistry, vol. 275, No. 34, pp. 25949-25958.
Kan et al. (1993) An Essential Heparin-Binding Domain in the Fibroblast Growth Factor Receptor Kinase, Science vol. 259:1918-1921 1-1.
Lee and Lander (1991) Analysis of Affinity and Structural Selectivity in the Binding of Proteins to Glycosaminoglycans: Development of Sensitive Electrophoretic Approach, Proc. Natl. Acad. Sci. USA,vol. 88 pp. 2768-2772, Apr. 1991, Biochemistry.
Lin et al (1999) Heparan Sulfate Proteoglycans Are Essential for FGF Receptor Signaling During Drosophila Embryonic Development, Development 126, 3715-3723 (1999) The Company of Biologists Limited.

(Continued)

*Primary Examiner* — Jacob Cheu

(74) *Attorney, Agent, or Firm* — Mark S. Cohen; Pearl Cohen Zedek Latzer, LLP

(57) ABSTRACT

The invention relates to methods for detecting and characterizing enzymatic modifications of oligosaccharides, such as heparan sulfate, and their interaction with binding partners, such as proteins, using an oligosaccharide-binding partner binding assay, such as a gel mobility shift assay. The instant invention relates to a rapid, convenient, sensitive and inexpensive method for identifying or studying oligosaccharide-binding partner interactions, identifying and characterizing structural features on oligosaccharides, identifying and characterizing binding partners, identifying agents capable of interfering with, enhancing, or facilitating the binding of an oligosaccharide to its binding partner, diagnosing conditions associated with altered oligosaccharide-binding partner binding, and generating oligosaccharide libraries and kits therefor.

23 Claims, 15 Drawing Sheets

(56) References Cited

OTHER PUBLICATIONS

Liu et al. (1999) Expression of Heparan Sulfate D-Glucosaminyl 3-0-Sulfotransferase Isoforms Reveals Novel Substrate Specificities, The American Society for Biochemistry and Molecular Biology, Inc, The Journal of Biological Chemistry vol. 274, No. 8 pp. 5185-5192.

Lindahl et al. (1998) Regulated Diversity of Heparan Sulfate, The American Society for Biochemistry and Molecular Biology, The Journal of Biological Chemistry vol. 273:24979-24982.

Lundin et al (2000) Selectively Desulfacted Heparin Inhibits Fibroblast Growth Factor-Induced Mitogenicity and Angiogenesis, The American Society for Biochemistry and Molecular Biology, The Journal of Biological Chemistry, vol. 275:24653-24660.

Lyon and Gallagher (1998) Bio-Specific Sequences and Domainis in Heparan Sulphate and The Regulation of Cell Growth and Adhesion, Gustav Fischer Verlag, Matrix Biology, vol. 17:485-493.

Maccarana et al (1993) Minimal Sequence in Heparin/Heparan Sulfate Required for Binding of Basic Fibroblast Growth Factor, The American Society for Biochemistry and Molecular Biology, Inc, The Journal of Biological Chemistry, vol. 268:23898-23905.

Mach et al. (1993) Nature of the Ineraction of Heparin With Acidic Fibroblast Growth Factor, American Chemical Society, Biochemistry vol. 32:5480-5489.

McKeehan et al (1999) Requirement for Anticoagulant Heparan Sulfate in the Fibroblast Growth Factor Receptor Complex, The American Society for Biochemistry and Molecular Biology, The Journal of Biological Chemistry, vol. 274:21511-21514.

Ornitz et al (1992) Heparin Is Required for Cell-Free Binding of Basic Fibroblast Growth Factor to a Soluble Receptor and for Mitogenesis in Whole Cells, Molecular and Cellular Biology, vol. 12 240-247.

Omitz et al (1995) FGF Binding and FGF Receptor Activation by Synthetic Hepran-Derived DI-AND Trisaccharides, Science vol. 268:432-436.

Parthasarathy et al (1994) Oligosaccharide Sequence of Endothelial Cell Surface Heparan Sulfate Proteoglycan With Affinity for Lipoprotein Lipase, The Journal of Biological Chemisty, vol. 33:10229-10248.

Wu et al. (2002) A New Strategy for Defining Critical Functional Groups on Heparan Sulfate, The FASEB Journal, vol. 16, 539-545.

Pantoliano, et al (1994), Multivalent Ligand-Receptor Binding Interactions in the Fibroblast Growth Factor System Produce a Cooperative Growth Factor and Heparin Mechanism for Receptor Demerization, Biochemistry, vol. 33, pp. 10229-10248.

Petitou et al (1998) Interactive of Heparin and Antithrombin III, The Role of O-Sulfate Groups, Eur J. Biochem . 176:637-640.

Plotnikov et al (1999) Structural Basis for FGF Receptor Dimerization and Activation, Cell Press, Cell, vol. 98:641-650.

Pye et al (2000) Regulation of FGF-1 Mitogenic Activity by Heparan Sulfate Oligosaccharides Is Depenent on Specific Structural Features: Differential Requirements for the Modulation of FGF-1 and FGF-2, Oxford University Press, Glycobiology vol. 10:1183-1192.

Rapraeger et al (1991) Requirement of Heparan Sulfate for Bfgf-Mediated Fibroblast Growth and Myoblast Differentiiation, Science vol. 252:1705-1708.

Rusnati et al (1999) Multiple Interactions of HIV-1 TAT Protein With Size-Definated Heparin Oligosaccharides, The Journal of Biological Chemistry, The American Society for Biochemistry and Molecular Biology, Inc, vol. 274:28198-28205.

Schlessinger et al (2000) Crystal Structure of a Ternary FGF-FGFR-Heparin Coplex Reveals A Dual Role for Heparin in FGFR Binding and Dimerization, Molecular Cell, vol. 6:734-750.

Shukla et at (1999) A Novel Role for 3-0-Sulfated Heparan Sulfate in Herpes Simplex Virus 1 Entry, Cell Press, Cell vol. 99:13-22.

Springer et at (1994) Indentificaion and Concerted Function of Two Receptor Binding Surfaces on Basic Fibroblast Growth Factor Required for Mitogenesis, The Journal of Biological Chemistry, The American Society for Biochemistry and Molecular Biology, Inc, vol. 269:26879-26884.

Steinfeld et al (1996) Stimularion of Fibroblast Growth Factor Receptor-1 Occupancy and Signaling by Cell Surface-Associated Syndecans and Glypican, The Journal of Biological Chemistry, The Rockefeller University Press, vol. 133:405-416.

Turnbull et al (1992) Identification of the Basic Fibroblast Growth Factor Binding Sequence in Fibroblast Heparan Sulfate, The Journal of Biological Chemistry, The American Socity for Biochemistry and Molecular Biology, Inc, vol. 267:10337-10341.

Venkataraman et al (1999) Sequencing Complex Polysaccharides, Science vol. 286:537-542.

Wang et al (1995) Alternately Spliced $NH_2$-Terminal Immunoglobulin-Like Loop I in the Ectodomain of the Fibroblast Growth Factor (FGF) Receptor 1 Lowers Affinity for Both Heparin and FGF-1, The Journal of Biological Chemistry, The American Society for Biochemistry and Molecular Biology, Inc, vol. 270:10231-10235.

Yayon et al (1991) Cell Surface, Heparin-Like Molcules Are Required for Binding of Basic Fibroblast Growth Factor to Its High Affinity Receptor, Cell Press, Cell, vol. 64:841-848.

Zhou et al (1997) Heparin-Dependent Fibroblast Growth Factor Activities: Effects of Defined Heparin Oligosaccharides, European Journal of Cell Biology, Wissenschaftliche Verlagsgesellschaft, Stuttgard 73:71-80.

Zhang et at (2001) 6-0 Sulfotransferase-1 Reprsetns A Critical Enzyme in the Anticoagulant Heparan Sulfate Biosynthetic Pathway, The Journal of Biological Chemistry, vol. 276 No. 45, Nov 9, pp. 42311-42321, 2001.

Zhang et al (2001) the Effect of Precursor Structures on the Action of Glucosaminyl 30 Sulfotransferase-1 and the Biosynthesis of Anticoagulant Heparan Sulfate, The Journal of Biological Chemistry, The American Society of Biochemistry and Molecular Biology, Inc, vol. 276, No. 31, Aug. 3, pp. 28806-28813, 2001.

International Search Report for International Application No. PCT/US02/31080 dated May 2, 2003.

* cited by examiner

METHODS FOR DETERMINING OLIGOSACCHARIDE BINDING

RELATED APPLICATIONS

This application is a continuation of U.S. patent application Ser. No. 10/263,338 filed on Oct. 1, 2002, now U.S. Pat. No. 7,754,432 claiming priority of U.S. Provisional Patent Application Ser. No. 60/326,270, filed Oct. 1, 2001 all of which are incorporated herein by reference in their entirety.

GOVERNMENT INTEREST STATEMENT

This invention was made with government support under Grant Nos. P01-HL66105 and P01-HL41484 awarded by the National Institutes of Health. The government has certain rights in this invention.

FIELD OF THE INVENTION

The invention relates to compositions and methods for oligosaccharide-binding partner binding assays, such as gel mobility shift assays, to reveal the structural features of oligosaccharides and/or their interactions with binding partners, such as proteins.

BACKGROUND OF THE INVENTION

Heparan sulfate (HS) and heparan sulfate proteoglycan (HSPG) play an important role in diverse biological systems, such as, i.e., proliferation, differentiation, homeostasis and viral pathogenesis (Perrimon and Bernfeld (2000) Nature 404: 725-728; Rosenberg et al. (1997) J. Clin. Invest. 99: 2062-2070; Shukla and Spear (2001) J. Clin. Invest. 108: 503-510). HSPG is present in almost every cell type in soluble form, as a component of the extracellular matrix (ECM), associated with plasma membranes, or segregated into intracellular granules (Lindahl et al. (1994) Thromb. Res. 75: 1-32). HSPGs modulate the biological activity of heparin-binding growth factors and cytokines through different mechanisms. For example, the optional binding of the growth factor to soluble, ECM-associated or cell-surface HSPGs may result in a fine control of the bioavailability of the protein. This is the case for TGF-β that binds betaglycan, a cell-associated PG (Massagué (1992) Cell 69: 1067-1070), and decorin (Yamaguchi et al. (1990) Nature (Lond.) 346: 281-284), which is present in the ECM, and for FGF-2 that binds basement membrane perlecan as well as cell-membrane syndecans (Avezier et al. (1994) Cell 79: 1005-1013; Samivirta et al. (1992) J. Biol. Chem. 267: 17606-17610). In addition, the association with HSPGs may stabilize the growth factor and protects it from proteolytic degradation (Saksela et al. (1988) J. Cell Biol. 107: 743-751; Sommer and Rifkin (1989) J. Cell. Physiol. 138: 215-220). Further, HSPGs modulate the access of growth factors to specific signaling receptors by different mechanisms (Ruoslahti and Yamaguchi (1991) Cell 64: 867-869). HSPGs can also control the intracellular fate of a growth factor (Rusnati et al. (1993) J. Cell. Physiol. 154: 152-161). In addition, transmembrane HSPGs themselves may transduce an intracellular signal, as suggested by the presence of highly conserved tyrosine residues in the C-terminal of all the members of the syndecan family, one of them fitting a consensus sequence for tyrosine phosphorylation. HSPGs may also activate an intracellular transduction signal by interacting directly with growth factor receptors (Revis-Gupta et al. (1991) Proc. Natl. Acad. Sci. U.S.A. 88: 5954-5958; Gao and Goldfarb (1995) EMBO J. 14: 2183-2190). (Special project Angiogenesis website http://www.med.unibs.it/~airc/).

Whatever the mechanism(s) of regulation of growth factor activity by HSPGs, the binding of the same growth factor to different HSPGs may have different biological consequences. This is the case for syndecan (Ausprunk et al. (1981) Am. J. Pathol. 103: 353-366; Chernousov and Carey (1993) J. Biol. Chem. 268: 16810-16814), betaglycan (Andres et al. (1992) J. Biol. Chem. 267: 5927-5930) and perlecan (Avezier et al. (1994) Cell 79: 1005-1013), which are all able to bind FGF-2 but with different effects. Syndecan inhibits the mitogenic activity of FGF-2 (Mali et al. (1993) J. Biol. Chem. 268: 24215-24222) while perlecan promotes FGF-2-induced cell proliferation and angiogenesis (Avezier et al. (1994) supra). Conversely, modifications of HSPG composition can regulate the sensitivity of the cell to different growth factors. This may be of particular relevance when the spatial and temporal control of the activity of different growth factors must be tightly enforced. This possibility is exemplified by the shift in cell-surface HSPG properties from an FGF-2- to an FGF-1-binding phenotype in murine neuronal cells during embryonic development (Nurcombe et al. (1995) Science 260: 103-106). (Special project Angiogenesis website http://www.med.unibs.it/~airc/).

HS is an unbranched polysaccharide polymer covalently attached to the core protein of proteoglycans. The myriad of functions attributed to HS is a consequence of its ability to interact with proteins and to affect their stability, conformation, concentration, and activity (Esko and Lindahl (2001) J. Clin. Invest. 108:169-173; Turnbull (1999) in *Cell Surface Proteoglycans in Signalling and Development, Vol. VI* (eds. Lander, A., Nakato, H., Selleck, S., Turnbull, J. & Coath, C.) p. 13-21). The binding interactions of HS with proteins regulate a number of cellular functions. For example, HS is critical for the entry into cells of herpes simplex virus type 1 (Shukla et al. (1999) Cell 99: 13-22); the HS chain of syndecan-3 is found to play a significant role in modulating feeding behavior in mice (Reizes et al. (2001) Cell 106: 105-116); and HS modulates the association between fibroblast growth factors (FGFs) and their receptors (FGFRs) (Spivak-Kroizman et al. (1994) Cell 79: 1015-1024; Pellegrini et al. (2000) Nature 407: 1029-1034; Schlessinger et al. (2000) Mol. Cell. 6: 743-750).

The biological significance of HS is also manifested at the whole animal level, where genes involved in HS biosynthesis are deficient (Forsberg and Kjellen (2001) J. Clin. Invest. 108: 175-180). For example, mice lacking glucosaminyl N-deacetylase/N-sulfotransferase 1 (NDST1) and HS 2-O sulfotransferase (2-OST), enzymes required for modifications of HS, die neonatally (Fan et al. (2000) FEBS Lett. 467: 7-11; Bullock et al. (1998) Genes Dev. 12: 1894-1906); a homozygous mutation of one of the HS polymerases, EXT1, in mice leads to embryonic lethality due to a failure to gastrulate (Lin et al. (2000) Dev. Biol. 224: 299-311); *Drosophila* with mutations of UDP-D-glucose dehydrogenase or NDST lack wingless activity as well as FGF and hedgehog signaling pathways (Bellaiche and Perrimon (1998) Nature 394: 85-88; Binari et al. (1997) Development 124: 2623-2632; Lin and Perrimon (1999) Nature 400: 281-284); and altered expression of HS proteoglycan leads to various human diseases, such as chondrodystrophic myotonia (Arikawa-Hirasawa et al. (2001) Nat. Genet. 27: 431-434) and hereditary bone disorders (McCormick et al. (1998) Nat. Genet. 19: 158-161).

Other oligosaccharides have a similar structure and dependence upon functional groups for binding to proteins. These include other GAGs, such as heparin and hyaluronic acid (HA); galactosaminoglycans, such as e.g., chondroitin-4-sulfate (C4S), chondroitin-6-sulfate (C6S), and dermatan sulfate (DS); and sulfated polylactosamines, such as, e.g., keratan sulfate (KS). Heparin, which is found in mast cells, has a similar structure to the sulfated regions of IIS. Chondroitin sulfates play a major role in the growth and repair of cartilage and consist of high viscosity mucopolysaccharides that act as the flexible connecting matrix between the protein filaments in cartilage to form a polymetric system. Chondroitin sulfates have been used in conjunction with glucosamine to treat osteoarthritis. A classification of some proteoglycans on the basis of their localization, core protein, and oligosaccharide content is provide in Table 1.

TABLE 1

Classification of proteoglycans on the basis of their localization and type of core protein

| Localization | GAG-chain | $M_r$ of the core protein (kD) | Principal members |
|---|---|---|---|
| ECM | HA, CS, KS | 225-250 | aggrecan, versican |
| Collagen-associated | CS, DS, KS | 40 | decorin, biglycan fibromodulin |
| Basement membrane | HS | 120 | perlecan |
| Cell-surface | HS, CS | $33^{[a]}$-$60^{[b]}$-$92^{[c]}$ | syndecans[a], glypican[b], betaglycan[c], CD44E, cerebroglycan |
| Intracellular granules | heparin, CS | 17-19 | Serglycin |

CS, chondroitin sulfate;
DS, dermatan sulfate;
KS, keratan sulfate;
HA, hyaluronic acid;
HS, heparan sulfate.
http://www.med.unibs.it/~airc/hspgs.html (Sep. 26, 2002).

Unlike DNA and proteins, in which sequence diversity is generated by nucleic acid and amino acid sequence variations, the sequence diversity of oligosaccharides such as HS is generated by heterogenous enzymatic modifications in the Golgi apparatus. HS is initially synthesized in the Golgi apparatus as non-sulfated copolymers attached to HS proteoglycan core proteins by sequential addition of D-glucuronic acid (GlcA) alternating with N-acetyl D-glucosamine (GlcNAc) catalyzed by HS polymerases. The oligosaccharide chain then undergoes various modification steps, which include N-deacetylation and N-sulfation of glucosamine, epimerization of GlcA to L-iduronic acid (IdoA), 2-O sulfation of uronic acid and 6-O sulfation and 3-O sulfation of glucosamine. All of the modification steps are catalyzed by different enzymes and the process is selective in terms of the position and the number of modifications in a chain, leading to extensive sequence diversity (Rosenberg et al. (1997) supra; Esko and Lindahl (2001) supra).

The heterogeneity of HS modifications may be due, for example, to differential expression or activity of these enzymes. With the exception of single isoforms for 2-O sulfotransferase (Kobayashi et al. (1997) J. Biol. Chem. 272: 13980-13985) and epimerase (Li et al. (1997) J. Biol. Chem. 272: 28158-28163), five isoforms have been cloned for 3-O sulfotransferase (3-OST) (Shworak et al (1999) J. Biol. Chem. 274: 5170-5184), four isoforms have been cloned for 6-O sulfotransferase (6-OST) (Habuchi et al. (1998) J. Biol. Chem. 273: 9208-9213) and four isoforms have been cloned for N-deacetylase/N-sulfotransferases (NDST) (Eriksson et al. (1994) J. Biol. Chem. 269: 10438-10443). Each isoform has its own substrate specificity, tissue expression pattern and, thus, unique function (Rosenberg et al. (1997) supra; Esko and Lindahl (2001) supra). For example, 3-OST-1 is specifically responsible for sulfating the antithrombin-III (AT-III) binding sequence and 3-OST-$3_A$ is critical for gD binding of herpes simplex virus (Shukla et al. (1999) supra). Tissue-specific and developmentally regulated expression of these isoforms produces HS chains with distinct sequences, enabling HS chains to interact with a broad array of protein ligands that modulate a wide range of biological functions involved in development, differentiation, homeostasis, and bacterial/viral entry.

Many proteins bind to HS (i.e., HS-binding proteins), including the proteins of the circulatory system, growth factors, receptors, adhesion proteins, enzymes, cytokines, chemokines, protease inhibitors and virus proteins. However, the oligosaccharide features (e.g., functional groups and their modification enzymes) required for binding to HS-binding proteins been defined for only a few proteins (Esko and Lindahl (2001) supra; Lindahl et al. (1998) J. Biol. Chem. 273: 24979-24982). For example, the way in which various HS proteoglycans (HSPG) discriminate among binding partners, e.g., heparin-binding growth factors, depends upon their different core proteins, the high heterogeneity of oligosaccharide composition, and on the possibility that both the protein moiety and oligosaccharide-chains may interact with different binding partners. For instance, betaglycan, an HSPG, can exist as a naked core protein and the presence and composition of the oligosacharide chains of betaglycan can be regulated in response to FGF-2 (Lopez-Casillas et al. (1991) Cell 67: 785-795). FGF-2 itself binds the oligosaccharide-chain of betaglycan while the core protein can interact with TGF-β (Andres et al. (1992) J. Biol. Chem. 267: 5927-5930). Also, the number and fine structure of HS chains in syndecan 1 vary in different tissues and in relation to cell differentiation (Bernfield and Sanderson (1990) Phil. Trans. R. Soc. Lond. 327: 171-186). Thus, different sulfated groups and distinct oligosaccharide sequences of the oligosaccharide chain are responsible for the binding to different growth factors (Special Project Angiogenesis website, http://www.med.unibs.it/~airc/, Sep. 26, 2002). Thus, HSPGs are characterized by a structural variability that appears to be highly regulated and that offers numerous possibilities for selective interactions with different growth factors, cytokines, and chemokines.

FGF and FGFR act on a wide spectrum of tissues and cell types and play critical roles in various biological processes, such as cell proliferation, differentiation, migration, embryonic development, tissue maintenance, angiogenesis, tumor growth and wound healing (Burgess and Maciag (1989) Ann. Rev. Biochem. 58: 575-606; Galzie et al. (1997) Biochem. Cell. Biol. 75: 669-685; Givol and Yayon (1992) FASEB J. 6: 3362-3369; Martin (1998) Genes Dev. 12: 1571-1586). Currently, there are 23 known FGFs and 5 types of FGFRs (Sleeman et al. (2001) Gene 271: 171-182). FGF1 and FGF2 were first to be isolated and were called acidic and basic FGF, respectively. Studies performed primarily on FGF2, have identified a stretch of basic residues in the polypeptide chain as participating in the heparin-binding site (Faham et al. (1996) Science 271: 1116-11120). FGFRs are members of the receptor tyrosine kinase superfamily. These receptors contain an intracellular tyrosine kinase domain, a trans-membrane region and an extracellular region containing three immunoglobulin (Ig)-like domains (Givol and Yayon (1992) supra). All FGFRs contain a heparin/HS binding site consisting of a stretch of 18 conserved residues in the second Ig-loop (Kan et al. (1993) Science 259: 1918-21). The amino-terminal Ig-like domain I is dispensable and receptor variants containing only the Ig-like domain II and III exhibit an equivalent degree of binding to FGFs as the variants containing all three domains (Givol and Yayon (1992) supra). All receptors show redundant specificity for ligand binding, where one receptor may bind to several FGFs and one FGF may bind to several receptors. FGF1 interacts with all the four known FGFRs and their isoforms. (Special project Angiogenesis website http://www.med.unibs.it/~airc/).

Direct involvement of heparan sulfate or heparin in the molecular association between FGF and its receptor is essential for FGF activated signal transduction (David (1993) FASEB J. 7: 1023-30; Kan et al. (1993) supra; Lundin et al. (2000) J. Biol. Chem. 275: 24653-24660; Spivak-Kroizman et al. (1994) Cell 79: 1015-1024). Heparan sulfate is required for the biological activity of FGF during *Drosophila* development (Lin et al. (1999) Development 126: 3715-3723). At normal concentrations, FGFs do not induce cell growth in HS deficient cells (Ornitz et al. (1992) Mol. Cell. Biol. 12: 240-247), but this induction can be restored by the addition of exogenous heparin (Rapraeger et al. (1991) Science 252: 1705-1708). The identification of HS as an active and essential component of the FGF:FGFR:HS signaling complex suggests that FGF activity and specificity may be modulated by HS and in turn, by enzymes that synthesize and degrade HS. It is of great pharmaceutical interest to design small oligosaccharides capable of modulating FGF signaling.

Although the importance of HS in FGF signaling is well documented, the exact structural roles of HS in the signaling complex are less well characterized. One key issue concerns the minimum size of HS required for FGF signaling. The size of HS reflects the spatial arrangement of FGF and FGFR and thus is critical for establishing a model for FGF signaling complex. So far, various signaling complex models have been proposed based on crystallographic studies, and, in each case, a different optimal length of HS was postulated (DiGabriele et al. (1998) Nature 393: 812-817; Pellegrini et al. (2000) supra; Plotnikov et al. (1999) Cell 98: 641-650; Schlessinger et al. (2000) Mol. Cell. 6: 743-750). Octasaccharide was proposed to be the minimal HS in some models, because shorter oligosaccharides would be incapable of connecting both ligand and receptor (Pellegrini et al. (2000) supra; Plotnikov et al. (1999) supra). In another case, heparin hexasaccharide was proposed to be sufficient to promote receptor dimerization (Schlessinger et al. (2000) supra). The shortest biologically active heparin oligosaccharide has been determined to be octasaccharide (Ornitz et al. (1992) supra), hexasaccharide (Gambarini et al. (1993) Mol. Cell. Biochem. 124: 121-129; Zhou et al. (1997) Eur. J. Cell. Biol. 73: 71-80), trisaccharide, and even disaccharide (Ornitz et al. (1995) Science 268: 432-436; Ostrovsky et al. (2002) J. Biol. Chem. 277: 2444-2453). These contradictory findings necessitate a more accurate method to determine the size of HS in FGF signaling complexes.

The stoichiometry of HS in the FGF molecular signaling complex has also been a subject of controversy. Intracellular signaling is believed to be initiated by receptor dimerization and trans-phosphorylation (Bellot et al. (1991) EMBO J. 10: 2849-2854; Heldin (1995) Cell 80: 213-223). In broad terms, three distinct models, with the ability for FGFR dimerization but different stoichiometry for FGF and HS have been proposed based on biochemical and crystallographical evidence (Delehedde et al. (2002) Biochem. J. 9: 366:235-244). In the first model, an FGF dimerizes two FGFRs, with a single HS chain binding both FGF and its receptor (Hsu (1999) Biochemistry 38: 2523-2534; Springer et al. (1994) J. Biol. Chem. 269: 26879-26884). In the second model, a single HS chain binds two FGFs, which in turn bind two FGFRs (Kwan et al. (2001) J. Biol. Chem. 276: 23421-23429; Pellegrini et al. (2000) supra). In the third model, one each of FGF, HS and FGFR first form an FGF:HS:FGFR complex, two of which then in turn dimerize (Schlessinger et al. (2000) supra).

Biological studies show that HSs from different tissues or developmental stages have different fine structures (Allen et al. (2001) J. Cell. Biol. 155: 845-858; Lindahl et al. (1998) supra) and can activate or even inhibit FGF signaling pathways (Pye et al. (2000) Glycobiology 10: 1183-1192; Zhang et al. (2001c) J. Biol. Chem. 276: 41921-41929). It is believed that this phenomenon is caused by switching of critical functional groups on the HSs (Lindahl et al. (1998) supra; Pye et al. (2000) supra). The critical functional groups on HS that interact with FGFs or FGFRs have been investigated previously. (Wu et al. (2002) supra; Guimond et al. (1993) J. Biol. Chem. 268: 23906-23914; Lyon and Gallagher (1998) Matrix Biol. 17: 485-493; Maccarana et al. (1993) J. Biol. Chem. 268: 23898-23905; Pye et al. (2000) supra; Turnbull et al. (1992) J. Biol. Chem. 267: 10337-10341; Zhou et al. (1997) supra) (Loo et al. (2001) J. Biol. Chem. 276: 16868-16876; McKeehan et al. (1999) J. Biol. Chem. 274: 21511-21514; Ostrovsky et al. (2002) supra). For example, 2-O sulfation at an iduronic acid are critical for FGF2 binding (Maccarana et al. (1993) supra) and 6-O-sulfate groups are important for FGFR4 binding (Loo et al. (2001) supra), but no information is available about the critical groups on HS mediating binding to FGF:FGFR binary complex. These critical groups may be different from those binding to individual FGFs and FGFRs, because the binding environment in the FGF:FGFR complex is different from that in individual FGFs or FGFRs (Plotnikov et al. (1999) supra). The study of these critical functional groups are important, because HS binding to the FGF:FGFR binary complex directly affects the formation of the FGF:HS:FGFR ternary complex, which is a prerequisite for the activation of FGF receptors.

There is little doubt that identifying the functional features on oligosaccharides will help to settle fundamental questions regarding development, physiology and the behavior process. However, neither molecular cloning nor sequencing technology are sufficient methods for obtaining large volumes of heterogenously modified oligosaccharides such as HS (Venkataraman et al. (1999) Science 286: 537-542). Such oligosaccharides may be heterogeneous in terms of sequence and size, and their binding partners may recognize motif structures rather than single, defined sequences. Most studies of heterogenously modified oligosaccharides require affinity purification to obtain a homogeneous population. However, the interaction between a heterogenously modified oligosaccharide and its binding partner(s) may be relatively weak and, because the source of heterogenously modified oligosaccharides is usually limited, it is almost impossible to obtain a homogeneous oligosaccharide sample by affinity purification. In addition, most current methods for studying oligosaccharide-protein interaction involve immobilization or chemical labeling of either component, which may introduce more difficulties and artifacts. Thus, a need exists for methods that can rapidly and accurately characterize the structural and/or functional features of a heterogenously modified oligosaccharide, such as HS, as well as to study oligosaccharide-binding partner interactions and to identify agents capable of interfering with, or enhancing, oligosaccharide-binding partner interactions and/or activity.

SUMMARY OF THE INVENTION

The instant invention relates to a rapid, convenient, sensitive and inexpensive method for identifying or studying oligosaccharide-binding partner interactions, identifying structural or functional features or groups on oligosaccharides, generating oligosaccharide libraries, identifying their binding partners, identifying inhibitors or enhancers of oligosaccharide-binding partner interactions and their analogs, and methods of treating individuals for conditions associated with aberrant oligosaccharide-binding partner binding interactions.

In the instant invention, a gel mobility shift assay (GMSA) was used to study oligosaccharide-binding partner interactions. GMSAs have been used for studying protein-DNA and protein-protein interactions and have proved very successful in identifying specific DNA sequences and their cognate proteins, e.g., transcription factors (Carthew et al. (1985) Cell 43: 439-448; Fried and Crothers (1981) Nucleic Acids Res. 9: 6505-6525). In the instant invention, heterogenously modified oligosaccharides, containing various numbers and combinations of functional groups, were created by in vitro modification and the effects of those modifications analyzed using GMSA.

In one aspect, the invention provides methods for detecting and/or characterizing binding between an isolated oligosaccharide and a binding partner by contacting an isolated oligosaccharide with a binding partner under conditions that allow binding of the oligosaccharide with the binding partner to form an oligosaccharide-binding partner complex and detecting the presence of the oligosaccharide-binding partner complex.

In another aspect, the invention provides diagnostic methods for detecting aberrant binding of an oligosaccharide to a binding partner in a subject's sample. In an embodiment, an oligosaccharide sample from a subject is combined with a binding partner and subjected to the GMSA of the invention. The ability of the subject's oligosaccharide to bind to the binding partner is assessed. In another embodiment, a binding partner sample from a subject is combined with one or more oligosaccharides and subjected to GMSA. The ability of the subjects' binding partner to bind to the oligosaccharide is assessed. A difference in the shift or retardation or amount of the bands on a GMSA as compared to that of a normal individual is indicative of an alteration in the oligosaccharide-binding partner binding in the subject, an alteration in the quantity or activity of oligosaccharide or binding partner in the subject, an alteration in the quantity or activity of an enzyme required for modification of the oligosaccharide, or a combination of the foregoing. It is contemplated that any defect that results in altered binding of oligosaccharide to a binding partner may be detected.

Once the altered oligosaccharide-binding partner binding is detected in a subject, additional experiments may be performed to determine the precise nature of the defect. In an embodiment, a subject's oligosaccharide sample may be supplemented with exogenous oligosaccharide prior to GMSA, to determine if oligoaccharide-binding partner binding can be recovered, thereby indicating that the subject's oligosaccharide is defective. In another embodiment, the subject's binding partner may be supplemented with exogenous binding partner prior to GMSA, wherein recovery of oligoaccharide-binding partner binding indicates a defect in the amount of binding partner. Where supplementation does not prove successful, this may indicate that the oligosaccharide and binding partner are not capable of binding, e.g., because the oligosaccharide is not properly modified, or because the sequence or structure of the oligosaccharide or binding partner is altered as compared to a normal control. In a further embodiment, the subject's oligosaccharide may be contacted with a modifying enzyme to determine whether the enzyme can recover the binding of the oligosaccharide to the binding partner (e.g., to restore the band shift). The methods of the invention may therefore be combined with other methods or assays to further characterize the diagnosis.

In another aspect, the invention provides methods for determining the requirement of a binding partner for a functional group on an oligosaccharide in order for the binding partner to bind to the oligosaccharide by contacting a modified oligosaccharide comprising at least one functional group with a binding partner under conditions that allow binding of the modified oligosaccharide with the binding partner to form a modified oligosaccharide-binding partner complex and detecting the presence of the modified oligosaccharide-binding partner complex. The presence of the modified oligosaccharide-binding partner complex is indicative of a requirement for the functional group on the oligosaccharide for binding to the binding partner.

In another aspect, the invention provides methods for identifying an agent capable of altering the binding of an oligosaccharide with a binding partner, by contacting an oligosaccharide with a binding partner under conditions that allow binding of the oligosaccharide with the binding partner to form an oligosaccharide-binding partner complex, contacting the oligosaccharide with a binding partner and an agent under conditions that allow binding of the oligosaccharide with the binding partner to form an oligosaccharide-binding partner complex, and detecting the presence of the oligosaccharide-binding partner complex. A difference in the amount of the oligosaccharide-binding partner complexes in the presence of the agent compared to the amount of the oligosaccharide-binding partner complexes in the absence of the agent is indicative that the agent inhibits or enhanced the binding of the oligosaccharide with the binding partner. A lower amount of the oligosaccharide-binding partner complexes in the presence of the agent compared to the amount of oligosaccharide-binding partner complexes in the absence of the agent is indicative that the agent inhibits the binding of the oligosaccharide with the binding partner. On the contrary, a higher amount of the oligosaccharide-binding partner complexes in the presence of the agent compared to the amount of oligosaccharide-binding partner complexes in the absence of the agent is indicative that the agent enhances or agonizes the binding of the oligosaccharide with the binding partner. In an embodiment, the methods of the invention are used to screen for agents that block the infection of a pathogen, such as a virus, bacteria, prion, fungi, yeast, or parasite (e.g. that inhibits binding of gD of Herpes Simplex Virus, or TAT of HIV-1 (e.g., the AIDS virus) to host cell). In another embodiment, the agent is an a pro-coagulant (e.g., that inhibits binding to AT-III). In another embodiment, the agent inhibits cell growth (e.g., that inhibits binding to and/or the activity of fibroblast growth factors and/or their receptors), inhibits cell adhesion (e.g., that inhibits fibronectin and L-selectin), inhibits inflammation (e.g., that inhibits binding to and/or the activity of cytokines and/or their receptors), and/or inhibits enzyme activity (e.g., that inhibits binding to and/or the activity of a matrix metalloproteases).

In an embodiment, the agent is an agonist or enhancer to oligosaccharide-binding partner binding. In an embodiment, the agent increases the affinity of the oligosaccharide for the binding partner. In another embodiment, the agent increased the half-life or decreases the turnover of either the oligosaccharide or the binding partner.

In another aspect, the invention provides a variety of methods for designing, testing and refining new molecules via rational drug design. For example, the invention provides a method that comprises the steps of: (a) providing a model, for example, a molecular model, having a functional locus of a binding partner, and (b) using the model to identify a candidate molecule having a surface complementary to the functional locus. Preferably, the candidate molecule stereochemically interfits and more preferably binds with the functional locus of the binding partner.

In a preferred embodiment, the method comprises one or more additional steps of: producing the candidate molecule identified in such a method; determining whether the candidate molecule, when produced, modulates (e.g., induces or reduces) oligosaccharide binding to and/or the activity of a binding partner; identifying a modified molecule; producing the modified molecule; determining whether the modified molecule, when produced, modulates the activity of the binding partner; and producing the modified molecule for use either alone or in combination with a pharmaceutically acceptable carrier.

In another aspect, the method comprises the additional step of producing the lead compound. After synthesis, the lead compound can be tested for biological activity, for example, modulation of oligosaccharide binding to and/or activity of a binding partner an in vitro assay according to the invention. Based on the results of such studies, it is possible to determine structure-activity relationships, which may then be used to design further modifications of the lead compound in order to improve a particular feature of interest. The modified lead compounds then can be produced and assessed for biological activity, as before. Once a compound of interest has been designed, synthesized and tested for activity, it may then be produced in commercially feasible quantities for use as a pharmaceutical.

In another aspect, the invention provides agents identified by the methods of the invention. Such agents are useful as therapeutics for treating conditions associated with altered or abnormal oligosaccharide-binding partner binding. Such agents may be an antibody, peptide, mimic or analog that can bind to the oligosaccharide and/or the binding partner.

In another aspect, the invention provides methods of treating a condition associated with altered oligosaccharide-binding partner binding, by administering an effective amount of an agent that inhibits or enhanced binding of the oligosaccharide to the binding partner.

In yet another aspect, the invention provides methods for determining the binding affinity for an oligosaccharide with a binding partner, by contacting an oligosaccharide with various quantities of a binding partner under conditions that allow binding of the oligosaccharide with the binding partner to form an oligosaccharide-binding partner complex, detecting the presence and/or quantity of the oligosaccharide-binding partner complexes for each quantity of binding partner, and calculating a dissociation constant for the oligosaccharide-binding partner complex.

In a further aspect, the invention provides methods for determining the minimal binding length of an oligosaccharide for a binding partner, by contacting samples of oligosaccharides of varying lengths with samples of a binding partner under conditions that allow binding of the oligosaccharides of varying lengths with the binding partner to form oligosaccharide-binding partner complexes, and detecting the presence of the oligosaccharide-binding partner complexes. Detection of an oligosaccharide-binding partner complex comprising the shortest oligosaccharide is indicative of the minimum binding length of the oligosaccharide for binding the binding partner. In an embodiment, the method further includes the step of modifying the oligosaccharide to contain at least one functional group.

In a further aspect, the invention provides methods for screening, identifying and/or characterizing a binding partner that binds to an oligosaccharide, by contacting an oligosaccharide with a candidate binding partner or a heterogenous mixture containing a candidate binding partner under conditions that allow binding of the oligosaccharide with the candidate binding partner to form an oligosaccharide-candidate binding partner complex, and detecting the presence of the oligosaccharide-candidate binding partner complex.

In another aspect, the invention provides methods of screening a library of oligosaccharides for binding to a candidate binding partner, by contacting an oligosaccharide library comprising a plurality of oligosaccharides with a candidate binding partner or a heterogenous mixture containing the candidate binding partner under conditions that allow binding of the oligosaccharides with the candidate binding partner to form an oligosaccharide-candidate binding partner complex, and detecting the presence of the oligosaccharide-candidate binding partner complex.

In an embodiment according to the invention, the oligosaccharides of the above methods contains between 2 and 300 saccharides, preferably 2 to 26 saccharides. In a preferred embodiment, the oligosaccharide comprises at least a portion of heparan sulfate or heparin. Alternatively, the oligosaccharide comprises chondroitin sulfate and/or keratan sulfate and/or dermatan sulfate and/or a portion of any of the foregoing.

In an embodiment, the oligosaccharide contains a detectable label. In another embodiment, the binding partner contains a detectable label. The detectable label may be a radioactive label or may be a non-radioactive label, such as biotin, fluoroscein, or green fluorescent protein or the like.

In an embodiment according to the invention, the oligosaccharide is chemically synthesized or manufactured in vitro. In another embodiment, the oligosaccharide is derived from an in vivo source, such as a tissue or cell sample. In an embodiment, the oligosaccharide contains at least one functional group. In another embodiment, the oligosaccharide is modified in vitro. For example, the oligosaccharide may be modified in vitro with 3-OST-1 and/or 6-OST-1. In another embodiment, the oligosaccharide may be modified in vitro with at least one sulfotransferase selected from the group consisting of 2-OST, 3-OST-1,3-OST-2, 3-OST-3A, 3-OST-4, 3-OST-5, 3-OST-6, 6-OST-1, 6-OST-2A, 6-OST-2B, and 6-OST-3. In another embodiment, the oligosaccharide is modified in vitro with an N-deacetylase/N-sulfotransferase (NDST), such as NDST1, NDST2, NDST3, and NDST4. In another embodiment, the functional group is added to the oligosaccharide in vivo or is naturally present on the oligosaccharide.

In an embodiment according to the invention, the binding partner is a protein, such as antithrombin III (AT-III), a growth factors, cytokines, chemokines, matrix metalloprotease, etc.: fibroblast growth factors (FGFs), vascular endothelial growth factor (VEGF), placental growth factor (PlGF), heparin-binding EGF-like growth factor, hepatocyte growth factor (HGF), transforming growth factor-beta (TGF-beta), platelet-derived growth factor (PDGF), pleiotrophin, platelet factor-4 (PF-4), interleukin-8 (IL-8), macrophage inflammatory protein-1 (MIP-1), interferon-g-inducible protein-10 (IP-10), interferon-gamma (IFN-gamma), and HIV-Tat transactivating factor. In another embodiment, the binding partner is a peptide, or an antibody, such as an autoantibody.

In an embodiment, the detecting step of the methods of the invention include subjecting the oligosaccharide-binding partner mixture, or modified oligosaccharide-binding partner mixture, to migration through a medium, such as a gel. In an embodiment, the detecting step comprises gel electrophoresis, e.g. vertical gel, horizontal gel, or capillary, and may include autoradiography. In a preferred embodiment, the detecting step comprises a gel mobility shift assay (GMSA).

In another aspect, the invention provides methods for identifying and/or characterizing an enzyme or other factor that modifies an oligosaccharide, by contacting an oligosaccharide with a candidate enzyme or a heterogenous mixture containing a candidate enzyme under conditions that allow the candidate enzyme to modify the oligosaccharide, contacting the modified oligosaccharide with a binding partner under conditions that allow binding of the oligosaccharide with the binding partner to form an oligosaccharide-binding partner complex, and detecting the presence of the oligosaccharide-binding partner complex, wherein the presence of the oligosaccharide-binding partner complex is indicative of the presence of an enzyme that is capable of modifying the oligosaccharide.

In another aspect, the invention provides kits for detecting the binding of an oligosaccharide to a binding partner, the kit containing an oligosaccharide and a binding partner for the oligosaccharide capable of serving as a control for detecting the presence of a second binding partner. In an embodiment, the kit contains at least one enzyme capable of modifying the oligosaccharide, In an embodiment, the oligosaccharide contains a detectable label.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which.

DETAILED DESCRIPTION OF THE INVENTION

Figure 1A:
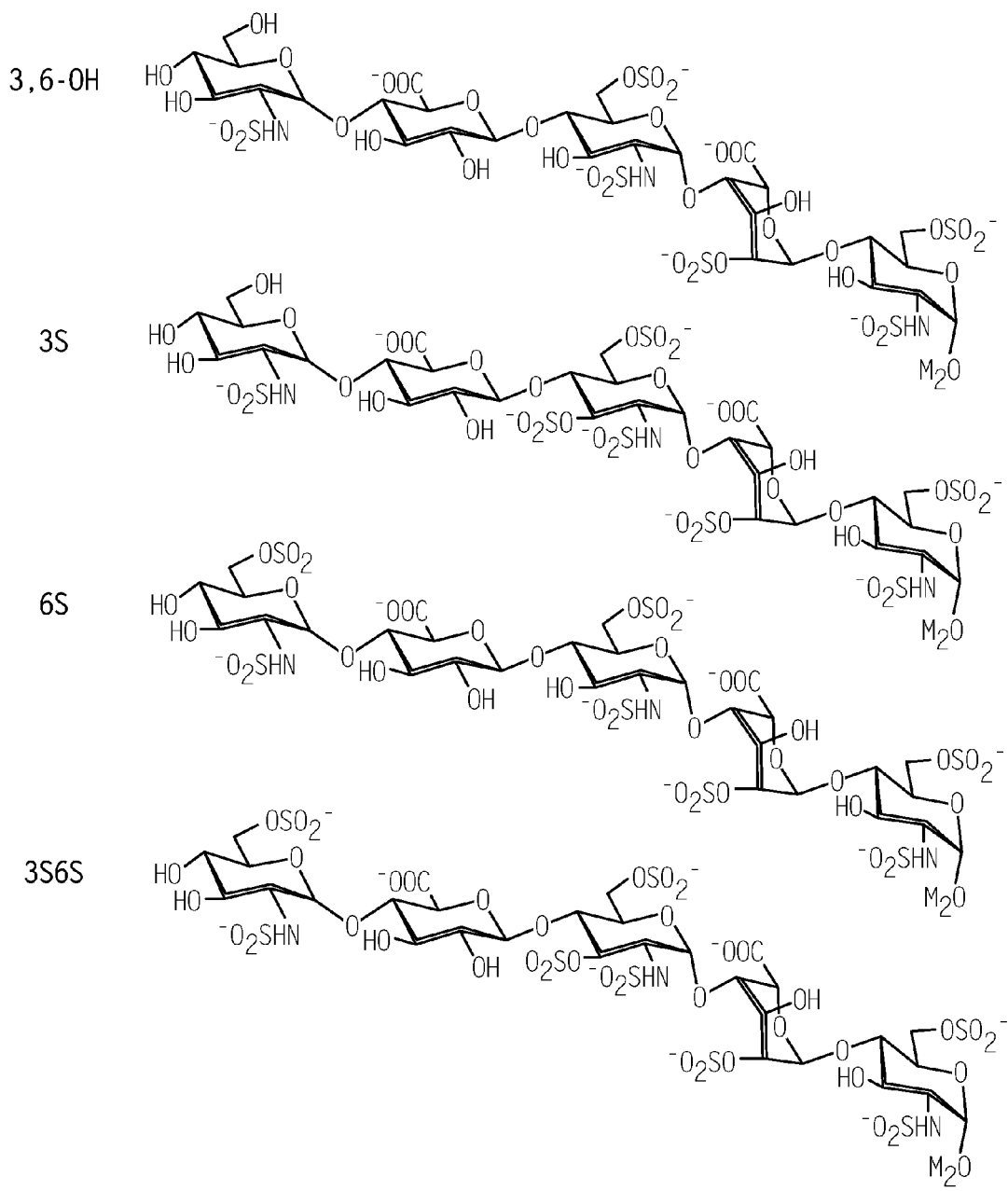
FIG. 1A illustrates that 3S, 6S and 3S6S sequences are pentasaccharides with sulfation at the critical 3-O, 6-O, and both positions respectively. 3,6-OH is desulfated at both positions. The critical 3-O, 6-O positions are shown as * and ●, respectively.

As used herein, the term "binding partner" refers to any molecule that binds to an oligosaccharide and can include a protein, peptide, oligosaccharide, antibody, etc.

As used herein, the term "computational chemistry" refers to calculations of the physical and chemical properties of a molecule.

As used herein, the terms "functional group", "structural group", "structural feature", and "functional feature" or the like are used interchangeably to refer to a specific atom or molecule that, when present in a biomolecule at a certain position on the biomolecule, provides the biomolecule with at least a specific chemical function or characteristic (e.g., for example, a binding characteristic, enzymatic activity, or other functional activity). A functional group may work in concert with or interact with another functional group to provide the biomolecule with the specific chemical function. Exemplary functional groups include sulfur groups, carboxylate groups, and hydroxyl groups.

As used herein, the terms "gel mobility shift assay" or "GMSA" and "electrophoretic mobility shift assay" or "EMSA" are used interchangeably to refer to the use of a gel to determine band retardation or shift, e.g., such polyacrylamide gel electrophoresis (PAGE) and, optionally, autoradiography, if a radioactive probe is used. However, the invention contemplates the use of any other binding assay that will detect a difference in the amount or size of a labeled oligosaccharide and/or binding partner that is not bound to a binding partner and/or oligosaccharide, respectively, and a labeled oligosaccharide and/or binding partner that not bound to a binding partner and/or oligosaccharide, respectively. Such binding assays include but are not limited to GMSA and capillary electrophoresis.

As used herein, the term "homology modeling" refers to the practice of deriving models for three-dimensional structures of macromolecules from existing three-dimensional structures for their homologues. Homology models are obtained using computer programs that make it possible to alter the identity of residues at positions where the sequence of the molecule of interest is not the same as that of the molecule of known structure.

As used herein, the term "isolated", when referring to an oligosaccharide, binding partner or other component of the instant invention, means that the component has been removed from its natural environment, e.g., the body; i.e., it is derived from the natural source.

As used herein, the terms "modify" or "modified" refer to the modification of oligosaccharides by enzymes such as sulfotransferases (e.g., NDSTs) and epimerases. Such modification may occur in vivo, e.g., in the Golgi apparatus or in any other location in the cell, such that functional groups, or their precursors or intermediates, are added, altered or removed from the oligosaccharide. In another embodiment, the modification of the oligosaccharide may occur in vitro.

As used herein, the term "molecular modeling" refers to a method or procedure that can be performed with or without a computer to make one or more models, and, optionally, to make predictions about structure activity relationships of ligands. The methods used in molecular modeling range from molecular graphics to computational chemistry.

As used herein, the terms "polysaccharide", "oligosaccharide", and "chain" are used interchangeably to refer to a polymer of glycosidically-linked saccharide residues. Although heparan sulfate is used as an exemplary oligosaccharide herein, many other oligosaccharides that bind to a binding partner maybe used or studied in the instant invention. Such other oligosaccharides include, but are not limited to, heparin, chondroitin sulfate, dermatan sulfate, and keratan sulfate.

Oligosaccharides such as heparin, heparan sulfate, chondroitin sulfate, dermatan sulfate, and keratan sulfate, of various lengths and with varying degrees of sulfation (e.g., 3-O or 6-O) or epimerization or other modification, may be obtained from commercial sources such as Iduron (Manchester, UK) or Sigma, or may be purified from a cell or tissue sample according to standard methods. For example, briefly, 5 ml of 6× pronase stock solution (1 mg/ml pronase (protease type XIV from *Streptomyces Griseus*); 0.24 M NaAc, 1.92 M NaCl pH 6.5) is added to each 150 mm dish of cells with 30 ml culture media and incubated at 37° C. overnight. The lysate is centrifuged at 3000 rpm 10 min and the supernatant collected. The supernatant is filtered and diluted 1:1.5 with water. 0.01% TX-100 is added to the supernatant and the pH adjusted to 6.5. The diluted supernatant is loaded onto a pre-equilibrated 1 ml DEAE-Sephacel column (pre-equilibrated with 12 ml of 0.25 M NaCl, 20 mM NaAc, 0.01% TX-100, pH 6.0. The column is washed with 30 ml of 0.25 M NaCl, 20 mM NaAc, 0.01% TX-100, pH 6.0. Glycosaminoglycans are eluted from the column with 5 ml 1M NaCl in 20 mM NaAc, pH 6.0. 10 ml of ethanol is added to 2.5 ml eluate in a 14 ml tube and incubated at 4° C. overnight. Precipitate is collected by centrifuging for 10 minutes as above. The pellet is washed with 1 ml 70% ethanol and precipitated by centrifuging for 7 minutes as above. The pellet is resuspended in 100 µl of water. 200 µl of the resuspended pellet is combined with 200 µl of 1 M NaBH$_4$, 0.5 M NaOH β-elimination solution and incubated at 4° C. for 24 hours. 5 µl of 1 mg/ml phenol red and 70 µl of HAc are added to the solution. After any bubbles have disappeared, the solution is neutralized by adding 2 M NaOH until the solution was red. 2 ml 1M NaCl in 20 mM NaAc, pH 6.0 and 10 ml cold ethanol were added and incubate at 4° C. for 3 hours. The precipitate is pelleted by centrifugation for 10 minutes as above. The pellet is washed with 1 ml 70% ethanol and the precipitate collected by centrifugation for 7 minutes as above. The pellet are dried and resuspended in 200 µl of water. For Chondroitinase ABC digestion, 200 µl of 2× digestion buffer (100 mM Tris, 100 mM NaAc, pH 8.0) and 4 µl of Chondroitinase ABC stock solution (10 mU/µl) is added to the GAG prep and incubated at 37° C. for 2 hours. The digestion of CS—C standard solution is checked at 232 nm. Theoretically, 0.5 ug/µl (the diluted concentration for measuring OD) of digested CS—C should generate 1.1 OD. If the digestion is completed, 400 µl of phenol:chloroform extraction solution (25:24:1) is added. The whole extraction process is undertaken at 4° C. in order to minimize the solubilized phenol in water phase, vortexed and centrifuged at 2000 rpm for 2 min. The water phase is transferred to a 15 ml tube. 2 ml 1M NaCl in 20 mM NaAc, pH 6.0 and 10 ml cold ethanol is added and incubated at 4° C. for 3 hours. The precipitate is collected by centrifuging 10 minutes as above. The pellet is washed with 1 ml 70% ethanol and centrifuged for 7 minutes as above and the pellet dried. The precipitate is resuspended with 500 µl of water and the HS concentration measured by the standard assay. Alternatively, the oligosaccharide may be synthesized in vitro according to standard methods.

The desulfating of an oligosaccharide may be achieved by treatment with a sulfatase according to standard methods (Matsuo et al. (1993) Carbohydr. Res 241: 209-15; Miller and Ax (1989) Gamete Res. 23(4): 451-65).

The basic disaccharide repeats of heparan sulfates, chondroitin sulfates, dermatan sulfates, and keratan sulfates are well known in the art. For example, heparin sulfate is composed of alternating N-acetyl D-glucosamine (GlcNAc) and D-glucuronic acid (GlcA) or IdoA. A pentamer of heparan sulfate may comprise GlcNAc-GlcA/IdoA-GlcNAc-GlcA/IdoA-GlcNAc or may comprise GlcA/IdoA-GlcNAc-GlcA/IdoA-GlcNAc-GlcA/IdoA. The composition of chondroitin sulfate is (GalNAc-GlcA)$_n$. The composition of dermatan sulfate is (GalNAc-GlcA/IdoA)$_n$. The composition of keratan sulfate is (Gal-GlcNAc)$_n$.

Binding partners may be prepared according to art known methods such as bacterial expression and protein purification, in vitro transcription and translation, peptide synthesis, monoclonal or polyclonal antibody preparation, affinity purification of proteins, etc.

Labeling of the oligosaccharide or binding partner may be achieved using standard methods of molecular and cellular biology, such as the use of a kinase to label an oligosaccharide with a radioactive group (Zhang et al. (2001a) J. Biol. Chem. 276: 28806-28813), fluorescent label, or enzymatic label. Labeling of an oligosaccharide may be performed as follows, for example. [$^{35}$S] 3'-phosphoadenosine 5'-phosphosulfate (PAPS) treatment of polysaccharides and in vitro modification is performed as previously described (Zhang et al. (2001a) supra; Wu et al. (2002) FASEB J. 16:539-545). Briefly, for a 25 µl reaction, 2 µg of substrate oligosaccharide and 12.5 µl of 2× buffer (50 mM MES (pH 7.0), 1% (w/v) Triton X-100, 5 mM MnCl$_2$, 5 mM MgCl$_2$, 2.5 mM CaCl$_2$, 0.075 mg/ml protamine chloride, 1.5 mg/ml bovine serum albumin) is combined with 70 ng of sulfotransferase and 2 µl [$^{35}$S]PAPS (~1×10$^7$ cpm), and the appropriate amount of water. The reaction is incubated at 37° C. for 20 minutes and stopped by heating to 75° C. for 3 minutes. The reaction is centrifuged at 10,000 g for 3 minutes and the superantant is used for GMSA. In an embodiment, more than one label may be used to label an oligosaccharide, e.g., if differential labeling of functional groups is desired. In addition, any labeling reaction known in the art that can label a binding partner may be used as an alternative to, or in addition to, the labeling of the oligosaccharide, e.g., if both a labeled oligosaccharide and/or a labeled binding partner are desired.

In an embodiment, a gel mobility shift assay (GMSA) can be used to analyze the binding of an oligosaccharide with a binding partner. For example, an HS oligosaccharide and binding partner AT-III may be used to characterize the functional groups required for binding of HS to AT-III. In addition, FGF1 and/or FGFR1 may be use to characterize the functional groups on HS required for binding of HS to FGF1 and/or FGFR1. Any other binding partner may be used, including FGF1, FGF2, FGFR1, FGFR2, FGFR3, and/or FGFR4. Further, a combination of binding partners may be used, such as, e.g., FGF1 and FGFR1.

The oligosaccharides of the invention may be of variable length, e.g., from 2-300 saccharides or longer if the length of the oligosaccharide does not adversely affect the shift of the oligosaccharide-binding partner complex formed. The composition of the oligosaccharide depends upon the binding partner or application of the invention.

The invention provides a method for determining the functional groups associated with an oligosaccharide and altering those functional groups. In an embodiment, the functional groups on a subject's oligosaccharides may not be completely modified (e.g., sulfated), thereby altering the oligosaccharide's ability to bind to a binding partner. The oligosaccharide may then be modified in vitro to determine whether the binding to the binding partner has been restored. The methods of the invention therefore provide both a diagnostic and a method for modeling a mimic for the oligosaccharide. The oligosaccharides may be modified, e.g., sulfated, epimerized, etc., to contain functional groups thereon. The number and/or combination of functional groups may represent or mimic the in vivo state of modification of the oligosaccharide. Alternatively, the number and/or combination of functional groups may be customized to study the effect of the presence or absence of additional, fewer or rearranged functional groups on the oligosaccharide. In an embodiment, the number and/or combination of functional groups may be incomplete or partial, such that the number and/or combination of functional groups mimics the natural state of an oligosaccharide at a certain point in the in vivo modification pathway, or in order to represent the number and/or combination of functional groups that are present on an oligosaccharide under certain conditions, e.g., at different stages of development, in a disease state, etc.

Sulfotransferases may be used to transfer a sulfate group onto the oligosaccharide. In an embodiment, the sulfotransferases may be used to label the oligosaccharide with a radiolabeled sulfate group. In another embodiment, the sulfotransferase may be used to transfer a non-radioactively labeled sulfate group to an oligosaccharide, such as biotin or green fluorescent protein or any such label known in the art. Sulfotransferases may be cloned and expressed in cells, e.g., COS cells or Baculovirus (Liu et al. (1999) supra; Zhang et al. (2001a) supra; Shworak et al. (1997) J. Biol. Chem. 272: 28008-28019) or may be obtained from commercial sources (e.g., PanVera, LLC, 501 Charmany Drive, Madison Wis.).

The invention further provides methods for assaying the binding of an oligosaccharide to a binding partner. In an embodiment, a gel mobility shift assay (GMSA) is used, as exemplified in Examples 1 and 7. A typical gel shift assay is performed as follows: for a 20 µl binding reaction, 10 ng of oligosaccharide (around 10,000 cpm) is mixed with an appropriate amount of a binding partner in binding buffer (12% glycerol, 20 mM Tris-HCl (pH 7.9), 100 mM KCl, 1 mM EDTA, and 1 mM DTT). The reaction is incubated at room temperature (23° C.) for 20 minutes. Multiple reactions are usually carried out at the same time. Half of the reaction (10 µl) is then applied to a 4.5% native polyacrylamide gel (with 0.1% bisacrylamide). The gel is run under 6 volts/cm for 1 to 2 hours using standard electrophoresis equipment, e.g., a SE 250 Mighty Small II gel apparatus (Hoefer Scientific Instruments, San Francisco). After the electrophoresis is finished, the gel is transferred to 3 mM paper and dried under vacuum. The dried gel is autoradiographed by a PhosphorImager 445SI (Molecular Dynamics, Sunnyvale, Calif.) or may be exposed to autoradiograph film using standard methods. The image can be analyzed by eye or with the use of densitometry, e.g., using NIH Image 1.60 software. The ratio between the bound and free oligosaccharides may be calculated according to the peak values and the concentrations of the oligosaccharides in the binding reaction may be derived. A dissociation constant may be calculated on the basis of concentrations of free and bound oligosaccharides and binding partner. The results of this experiment may reveal whether an oligosaccharide binds to a binding partner, may identify a binding partner that binds to a particular oligosaccharide, may identify an oligosaccharide that binds to a particular binding partner, or may identify a mimic that inhibits binding of the oligosaccharide to a binding partner, e.g., mimics the oligosaccharide or mimics the binding partner. The methods of the invention may also provide a means for studying, characterizing, diagnosing, inhibiting or enhancing the binding of a oligosaccharide with one or more binding partners or studying or characterizing the functional groups on the oligosaccharide, or designing mimics therefor. In addition, the methods of the invention may be used to detect altered oligosaccharide-binding partner binding that is indicative of a condition or disease associated with an alteration in the expression or modification of an oligosaccharide, binding partner, and/or modifying enzyme, which alteration may manifest itself in an alternative from normal oligosaccharide-binding partner binding.

Figure 7:
FIG. 7 shows a diagrammatical representation of the oligosaccharide modifications of the invention as described in Example 3, 4 and 6. The first three steps of modification occur in vivo prior to isolation of the oligosaccharide from a tissue or cell. These modifications are followed by an in vitro sulfation step, affinity purification and oligosaccharide-binding partner analysis.

The invention provides methods for studying or characterizing the binding affinity of an oligosaccharide for one or more binding partners. For example, the affinity of HS for proteins is essential for the functions of HS and alterations thereof may indicate a disease state in which the affinity of HS for its binding partner is altered. To measure the affinity for an oligosaccharide for a binding partner, an oligosaccharide is incubated with varying amounts of a binding partner, as exemplified in Examples 2 for the binding partner AT-III and in FIG. 7 for the binding partners FGF1 and FGFR1. In a typical experiment, the same amount of an oligosaccharide (e.g., 120 ng, with a specific activity of $3.3 \times 10^6$ cpm/µg) is incubated with various amounts of a binding partner (e.g., 0, 25, 50, 100, 250, 500, 1000, 2500, 5000 and 10000 ng). The reactions are then analyzed by, e.g., GMSA and autoradiography and a dissociation constant $K_d$ is calculated according to standard methods.

The invention provides methods fore determining the minimal length of an oligosaccharides required for binding to a binding partner, such as HS. Such information may be used to design mimics or homologues that can specifically target the binding sites for oligosaccharides on binding partners and/or the binding sites for binding partners on oligosaccharides to treat a disease or other condition associated with oligosaccharide-binding partner binding. For example, the minimal FGF-2-binding sequence in HS has been identified as a pentasaccharide which contains the disaccharide units IdoA(2-OSO$_3$)-GlcNSO$_3$ or IdoA(2-OSO$_3$)-GlcNSO$_3$(6-OSO$_3$) (Maccarana et al. (1993) J. Biol. Chem. 268: 23898-23905). As an illustration of the use of the methods of the invention, the minimal binding length of HS for binding to AT-III was determined, as described in Example 3 and the minimal binding length of HS for binding to FGF1 and/or FGFR1 was determined, as described in Example 8. Briefly, an oligosaccharide ladder is radiolabeled, e.g., with [$^{35}$S] using 3-OST-1. The oligosaccharides may or may not be modified, e.g., already 3-O and 6-O sulfated. The labeled oligosaccharides are incubated with an amount of binding partner and separated by electrophoresis on a gel, e.g., PAGE gel. The gel is analyzed to determine what lengths of labeled oligosaccharide band are shifted (i.e., retarded) in the gel. The instant invention provides rapid methods for determining the minimum number of saccharide units required for binding of an oligosaccharide to a binding partner.

Figure 4B:
FIG. 4B shows the results of a binding assay of an 18-mer oligosaccharide modified with 6-OST-1 and shifted with increasing amounts of AT-III.
Figure 4B:
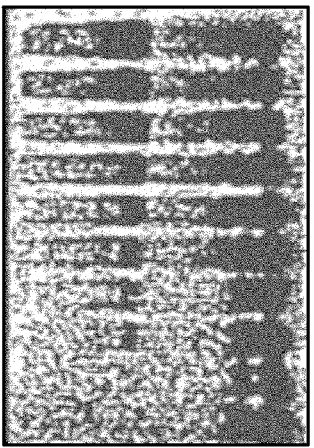
Figure 4D:
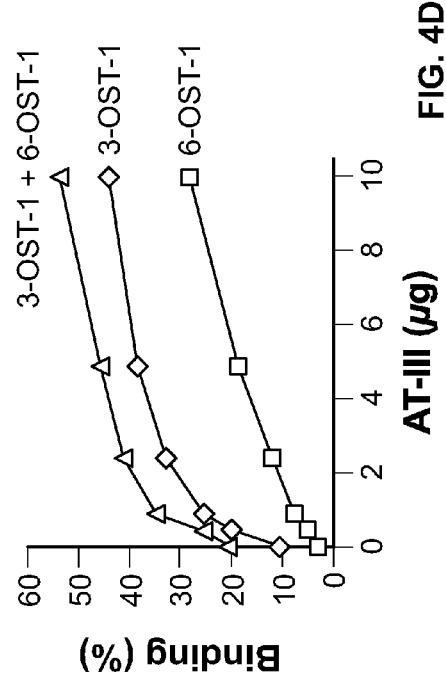
FIG. 4D shows the binding curve of the modified 18-mer oligosaccharide with 3-OST-1,6-OST-1, or 3-OST-1 and 6-OST-1.

The invention provides methods for determining and/or characterizing sequence-specific interactions between an oligosaccharide and a binding partner, e.g., whether a fraction of a modified oligosaccharide can bind to a binding partner. Using GMSA, the presence of sequence-specific oligosaccharide-binding partner interactions can be determined. As demonstrated in FIGS. 4A-4D, and 10, an oligosaccharide may be modified with various combinations of functional groups and binding to a binding partner analyzed. For example, an octadecamer was radiolabeled with 3-OST-1 and/or 6-OST-1, and the modified octadecamers were subject to GMSA after incubation with AT-III. Various amounts of the octadecamer was shifted depending upon the functional groups that were added to the oligosaccharide. For the 6-OST-I modification, about 25% of the octadecamer could bind to AT-III; for 3-OST-1 modification, about 40% of the octadecamer could bind to AT-III; and for the 3-OST-1 and 6-OST-1 double modification, about 50% of the octadecamer could bind to AT-III (FIG. 4D).

Since Yayon et al. (Yayon et al. (1991) Cell 64: 841-848) first demonstrated the importance of HSPG for high affinity FGF2:FGFR1 binding, a large amount of data has been produced, indicating that HSPG is essential for FGF signaling (Bernfield et al. (1999) Ann. Rev. Biochem. 68: 729-777; Gallagher (2001) supra; Lin et al. (1999) supra; Rapraeger et al. (1991) supra; Steinfeld et al. (1996) J. Cell. Biol. 133: 405-16). Later, Heparin and HS have since proved to be an essential component of FGF signaling complex (Bernfield et al. (1999) supra; Gallagher (2001) supra; Pellegrini et al. (2000) supra; Schlessinger et al. (2000) supra). The invention demonstrated that the size and the functional groups of HS can affect the formation of the signaling complex and thus the activation of FGFR. The methods of the invention demonstrate that heparin oligosaccharides as short as dp4 were able to initiate the ternary complex formation and activate the signaling pathway. The methods of the invention were used to demonstrate that the molar ratio of oligosaccharide, FGF1 and FGFR1 in the signaling complex was determined to be 1:1:1 (Example 9). The interaction of HS with FGF1 and FGFR1 in the complex was not a simple addition of the individual interactions of HS/FGF1 and HS/FGFR1 (Example 9). N- and some O-sulfations were critical for the formation of the FGF1:HS:FGFR1 signaling complex, which again was a prerequisite for FGF1 stimulated cell growth (Examples 10 and 11).

Figure 5:
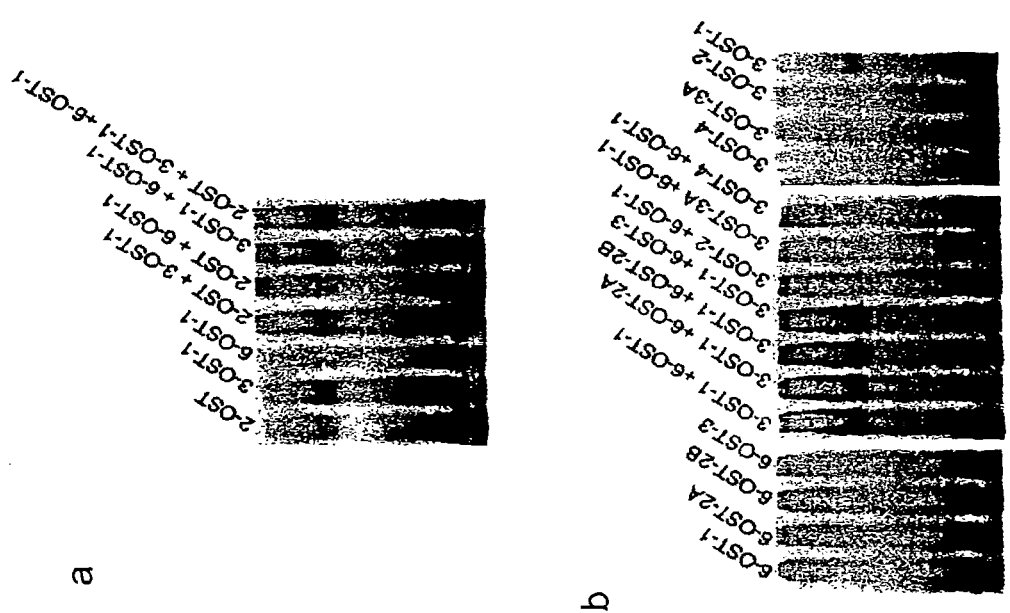
FIG. 5A shows the reconstitution of AT-III binding sites on completely desulfated and N-resulfated heparin (DSNS). DSNS was modified with 2-OST, 3-OST-1, 6-OST-1 or different combinations of those enzymes and then approximately the same amount of radioactivity (20,000 cpm) for each modification was used in binding assays with AT-III. In each assay, 5 µg of AT-III was used.
FIG. 5B shows the reconstitution of AT-III binding sites on completely desulfated and N-resulfated heparin (DSNS). The results show that substitution of 3-OST-1 with other 3-OST isoforms resulted in loss of binding to AT-III, but substitution of 6-OST-1 with other 6-OST isoforms did not change the binding affinity for the DSNS of AT-III.

The invention also provides methods for identifying and/or characterizing enzymes that are capable of modifying oligosaccharides. The methods of the invention described in Example 5, for example, may be used to then test the ability of the enzyme to modify oligosaccharides in vitro. FIG. 5B shows the reconstitution of AT-III binding sites on DSNS using one or more of the sulfotransferases 3-OST-1, 6-OST-1, 6-OST-2A, 6-OST-2B, or 6-OST-3. In an embodiment, the invention provides diagnostic methods for detecting an alteration in enzyme levels or activity in a subject. A subject's oligosaccharide or binding partner sample may be subjected to GMSA in order to detect binding. In the event of a decrease in binding as compared to normal controls, the oligosaccharide or binding partner can be contacted with an enzyme of interest, followed by GMSA. An improvement in the binding of the oligosaccharide or binding partner indicates that the subject may express lower levels of enzyme or that the activity of the enzyme is decreased compared to normal.

The invention also provides methods for generating and characterizing oligosaccharide libraries by generating desired lengths of an oligosaccharide of interest and modifying the oligosaccharide with one or more modifying enzymes, e.g., sulfotransferases. The library can then be characterized by determining which binding partners can bind the library.

In a natural sample of HS, or HS library generated by in vitro modifications, only the oligosaccharides bound to proteins are revealed as shifted bands in GMSA. With the instant invention, it is possible to determine the critical functional groups on any protein-binding oligosaccharide such as, e.g., HS, to establish whether those groups work in a cooperative manner, and to reveal the relationship between modification enzymes, functional groups and biological functions. After the identification and/or characterization of the structural features of HS recognized by a certain protein, it will be possible to generate one or more oligosaccharides with the same, or enhanced (i.e., capable of stronger or more prolonged binding to the binding partner), features by in vitro modification and to use the oligosaccharide as a drug, e.g., to block biological activities, such as the binding of gD of Herpes Simplex virus (Shukla et al. (1999) supra) or Tat of human immunodeficiency virus (Rusnati et al. (1999) J. Biol. Chem. 274: 28198-28205) to the HS receptors on host cells. Because homogeneous HS is not required and because of the great sensitivity of GMSA, it is possible to prepare in vivo labeled HS from tissues, e.g., from different development stages, different tissue types, different individuals or different species, and to determine how a specific protein-interacting HS forms and functions.

The invention further provides kits for use in diagnostics or prognostic methods for diseases or conditions associated with abnormal oligosaccharide-binding partner binding, or for determining which therapeutic should be administered to a subject, for example, by detecting the presence of oligosaccharide or binding partner in a biological sample, such as, e.g., a blood, saliva, ascites, or fecal sample. The kit may detect abnormal levels of oligosaccharides and/or binding partners or abnormal binding of the oligosaccharide to a binding partner. In an embodiment, the kit contains at least one oligosaccharide. In another embodiment, the kit contains a library of oligosaccharides. The oligosaccharides may by modified (e.g., sulfated or epimerised), depending upon the application and upon the target binding partner. The oligosaccharides may also be of different lengths or compositions (HS, chondroitin sulfate, dermatan sulfate, keratan sulfate). The kit may also comprises at least one binding partner or a portion thereof (e.g., the binding site). The kit may also contain and antibody for detecting an oligosaccharide or a binding protein. In an embodiment of the invention, the kit detects autoantibodies specific for an oligosaccharide and/or a binding partner. In another embodiment, the kit comprises a labeled compound or agent capable of detecting oligosaccharides and/or binding partners in a biological sample or reagents for comparing the amount of oligosaccharides and/or binding partners in the sample with a standard control or may provide labeling reagents one or more of the components of the invention. The compound or agent can be packaged in a suitable container. The kit can further comprise instructions for using the kit to detect oligosaccharides or binding partners.

Molecular Modeling

The invention also provides methods for producing a mimic that will interfere with or enhance the binding of an oligosaccharide with a binding partner. For example, heparan sulfate PGs (HSPGs), are involved in the modulation of the neovascularization that takes place in different physiological and pathological conditions. This modulation occurs through the interaction of HSPGs with angiogenic growth factors or with negative regulators of angiogenesis. The information obtained regarding the interaction between HS and an angiogenic growth factor, for example, can be used to design synthetic GAG analogs endowed with angiostatic properties. Angiogenesis-related HS binding partners include the following growth factors, cytokines, and chemokines: fibroblast growth factors (FGFs), vascular endothelial growth factor (VEGF), placental growth factor (PlGF), heparin-binding EGF-like growth factor, hepatocyte growth factor (HGF), transforming growth factor-beta (TGF-beta), platelet-derived growth factor (PDGF), pleiotrophin, platelet factor-4 (PF-4), interleukin-8 (IL-8), macrophage inflammatory protein-1 (MIP-1), interferon-g-inducible protein-10 (IP-10), interferon-gamma (IFN-gamma), and HIV-Tat transactivating factor.

The instant invention provides methods of screening for natural inhibitors of oligosaccharide-binding partner binding. For example, a number of inhibitors of angiogenesis have been identifies, such as protamine, chemokines (e.g., PF-4, IP-10), D-gluco-D-galactan sulfate (DS-4152 or tecogalan), alpha-2-macroglobulin. In addition, a number of synthetic inhibitors have been identified, including suramin derivatives, pentosan polysulfate, and phosphorothioate oligodeoxynucleotides (http://www.med.unibs.it/~airc/). The instant invention provides a rapid method for screening and characterizing these and other agents that function as inhibitors of angiogenesis, for example.

It is also contemplated that the identification of the active site of a binding partner protein identified and/or characterized by the invention, whether derived from one or more of X-ray crystallography, molecular modeling, homology modeling or molecular replacement, may be used in rational drug design (RDD) to design a novel molecule of interest, for example, novel modulators (for example, inducers, mimetics or inhibitors) of oligosacharide or binding partner function. Furthermore, it is contemplated that, by using the principles disclosed herein, the skilled artisan can design, make, test, refine and use novel inhibitors or enhancers specifically engineered to reduce, disrupt, or otherwise inhibit or enhance binding partner function in an organism or species of interest. For example, by using the principles discussed herein, the skilled artisan can engineer new molecules that specifically target and inhibit a binding partner such as AT-III or FGF1 and/or FGFR1, for example. As a result, by defining the binding site of an oligosaccharide on one or more binding partners the skilled artisan may design new reagents that can inhibit or enhance the activity of an oligosaccharide and/or binding partner(s). For example, the ternary binding site of FGF1 and FGFR1 is the site of cell signalling and biological activity. This site is critical to designing inhibitors.

It is contemplated that RDD can be facilitated most readily via computer-assisted drug design (CADD) using conventional computer hardware and software known and used in the art. The candidate molecules may be designed de novo or may be designed as a modified version of an already existing molecule, for example, a pre-existing inhibitor, using conventional methodologies. Once designed, candidate molecules can be synthesized using standard methodologies known and used in the art. Following synthesis, the candidate molecules can be screened for bioactivity, for example, by their ability to reduce or inhibit binding partner and/or oligosaccharide function, and their ability to interact with or bind a binding partner and/or oligosaccharide. Based in part upon these results, the candidate molecules may be refined iteratively using one or more of the foregoing steps to produce a more desirable molecule with a desired biological activity. The resulting molecules can be useful in treating, inhibiting or preventing infection by a pathogen in any organism, angiogenesis, inflammation, cancer, or any condition associated with alter or abnormal oligosaccharide-binding partner binding.

It is contemplated that the design of candidate molecules, as discussed in detail hereinbelow, can be facilitated using conventional computers or workstations, available commercially from, for example, Silicon Graphics Inc. and Sun Microsystems, running, for example, UNIX based, Windows NT on IBM OS/2 operating systems, and capable of running conventional computer programs for molecular modeling and rational drug design.

The computer-based systems of the invention preferably comprise a data storage means having stored therein a oligosaccharide and/or binding partner or fragment sequence and/or atomic co-ordinate/X-ray diffraction data and the necessary hardware means and software means for supporting and implementing an analysis means. As used herein, "a computer system" or "a computer-based system" refers to the hardware means, software means, and data storage means used to analyze the sequence, X-ray diffraction data, and/or atomic co-ordinates of the invention. As used herein, the term "data storage means" is understood to refer to any memory which can store sequence data, atomic co-ordinates, and/or X-ray diffraction data, or a memory access means which can access manufactures having recorded thereon the atomic co-ordinates of the present invention.

In one embodiment, a binding partner, or at least a portion thereof, amino acid and nucleic acid sequence, X-ray diffraction data and/or atomic co-ordinates of the binding protein are recorded on computer readable medium. As used herein, the term "computer readable medium" is understood to mean any medium that can be read and accessed directly by a computer. Such media include, but are not limited to: magnetic storage media, such as floppy discs, hard disc storage medium, and magnetic tape; optical storage media such as optical discs or CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon an amino acid and/or nucleotide sequence, X-ray diffraction data, and/or atomic co-ordinates of a binding protein.

As used herein, the term "recorded" is understood to mean any process for storing information on computer readable medium. A skilled artisan can readily adopt any of the presently known methods for recording information on computer readable medium to generate manufactures comprising amino acid or nucleotide sequence data of the present invention.

By providing a computer readable medium having stored thereon the nucleic acid sequence or amino acid sequence of a binding partner or oligosaccharide binding site thereon, a skilled artisan can routinely access the sequence, and/or atomic co-ordinates, to model an oligosaccharide, binding partner or oligosaccharide binding site thereon, a subdomain thereof, mimetic, or a ligand thereof. Computer algorithms are publicly and commercially available which allow a skilled artisan to access this data provided in a computer readable medium and analyze it for molecular modeling and/or RDD. See, e.g., *Biotechnology Software Directory*, MaryAnn Liebert Publ., New York, N.Y. (1995).

Although computers are not required, molecular modeling can be most readily facilitated by using computers to build realistic models of a binding partner or oligosaccharide binding site thereon. Molecular modeling also permits the modeling of new smaller molecules, for example ligands, agents and other molecules, that can bind to an oligosaccharide, a binding partner or the oligosaccharide binding site thereon. The methods utilized in molecular modeling range from molecular graphics (i.e., three-dimensional representations) to computational chemistry (i.e., calculations of the physical and chemical properties) to make predictions about the binding of the smaller molecules or their activities; to design new molecules; and to predict novel molecules, including ligands such as drugs, for chemical synthesis.

For basic information on molecular modeling, see, for example, M. Schlecht, *Molecular Modeling on the PC* (1998) John Wiley & Sons; Gans et al., *Fundamental Principals of Molecular Modeling* (1996) Plenum Pub. Corp.; N. C. Cohen, ed., *Guidebook on Molecular Modeling in Drug Design* (1996) Academic Press; and W. B. Smith, *Introduction to Theoretical Organic Chemistry and Molecular Modeling* (1996). U.S. patents which provide detailed information on molecular modeling include, for example: U.S. Pat. Nos. 6,093,573; 6,080,576; 6,075,014; 6,075,123; 6,071,700; 5,994,503; 5,884,230; 5,612,894; 5,583,973; 5,030,103; 4,906,122; and 4,812,12.

One approach to RDD is to search for known molecular structures that might bind to a site of interest. Using molecular modeling, RDD programs can look at a range of different molecular structures of molecules that may fit into a site of interest, and by moving them on the computer screen or via computation it can be decided which structures actually fit the site well (William Bains (1998) *Biotechnology from A to Z*, second edition, Oxford University Press, p. 259).

An alternative but related approach starts with the known structure of a complex with a small molecule ligand and models modifications of that small molecule in an effort to make additional favorable interactions with an oligosaccharide, binding partner or oligosaccharide binding site.

The present invention permits the use of molecular and computer modeling techniques to design and select novel molecules, such anti-angiogenesis agents, antiinflammatory agents, or other therapeutic agents, that interact with binding partner or oligosaccharide binding site.

The skilled artisan can generate atomic co-ordinates via, for example, molecular modeling using, for example, homology modeling and/or molecular replacement techniques, that together define at least a portion of a model of an oligosaccharide, a binding partner or oligosaccharide binding site from another species of interest. By using the foregoing atomic co-ordinates, the skilled artisan can design inhibitors or enhancers of an oligosaccharide, binding partners or their interactions with oligosaccharides that may be tailored to be effective against an oligosaccharide or binding partners from one or more species but which have little or no effect on binding partners of other species. Such inhibitors may be competitive inhibitors. As used herein, the term "competitive inhibitor" refers to an inhibitor that binds to the active form of an oligosaccharide, binding partner or oligosaccharide binding site at the same sites as other oligosaccharides, thus directly competing with them. The term "active form" of a oligosaccharide, binding partner or oligosaccharide binding site refers to binding partner or oligosaccharide binding site in a state that renders it capable of binding to a oligosaccharide. Competitive inhibition can be reversed completely by increasing the oligosaccharide or other substrate concentration.

This invention also permits the design of molecules that act as uncompetitive inhibitors of oligosaccharide-binding partner binding. As used herein, the term "uncompetitive inhibitor" refers to a molecule that inhibits the functional activity of a oligosaccharide by binding to a different site on the binding partner than does other oligosaccharides or other substrates. Such inhibitors can often bind to the binding partner-oligosaccharide complex and not to the oligosaccharide, binding partner or oligosaccharide binding site by itself. Uncompetitive inhibition cannot be reversed completely by increasing the oligosaccharide concentration. These inhibitors may bind to, all or a portion of, the active sites or other regions of the oligosaccharide, binding partner or oligosaccharide already bound to its oligosaccharide and may be more potent and less non-specific than known competitive inhibitors that compete for the binding partner or oligosaccharide binding site or for binding to a binding partner or oligosaccharide binding site.

Similarly, non-competitive inhibitors that bind to and inhibit an oligosaccharide, a binding partner, whether or not it is bound to another chemical entity, may be designed using the binding partner or oligosaccharide binding site or complexes comprising the binding partner or oligosaccharide binding site of this invention. As used herein, the term "non-competitive inhibitor" refers to an inhibitor that can bind to either the free or oligosaccharide bound form of the binding partner.

Those of skill in the art may identify inhibitors as competitive, uncompetitive, or non-competitive by computer fitting enzyme kinetic data using standard equation according to Segel, I. H., (1975) *Enzyme Kinetics: Behaviour and Analysis of Rapid Equilibrium and Steady-State Enzyme Systems*, (Wiley Classics Library). It should also be understood that uncompetitive or non-competitive inhibitors according to the present invention may bind the same or different binding sites.

The invention permits the skilled artisan to identify target locations in an oligosaccharide or binding partner that can serve as a starting point in rational drug design. As a threshold matter, the invention permits the skilled artisan to identify specific regions within an oligosaccharide or binding partner that are involved with binding of an oligosaccharide to a binding partner. Furthermore, invention permit a skilled artisan to further identify portions of these regions that are conserved or are not conserved between different organisms.

It is contemplated that candidate molecules that inhibit oligosaccharide-binding partner binding can be designed entirely de novo or may be based upon a pre-existing inhibitor. Either of these approaches can be facilitated by computationally screening databases and libraries of small molecules for chemical entities, agents, ligands, or compounds that can bind in whole, or in part, to oligosaccharides and/or their binding partners. In this screening, the quality of fit of such entities or compounds to the binding site or sites on the oligosaccharide or binding partner may be judged either by shape complementarity or by estimated interaction energy (Meng et al. (1992) J. Comp. Chem. 13: 505-524).

The design of molecules that bind to or inhibit the functional activity of an oligosaccharide and/or a binding partner according to this invention generally involves consideration of two factors. First, the molecule must be capable of physically and structurally associating with the oligosaccharide and/or its binding partners. Non-covalent molecular interactions important in the association of oligosaccharide and/or binding partners with the molecule, include hydrogen bonding, van der Waals and hydrophobic interactions. Second, the molecule must be able to assume a conformation that allows it to associate with the oligosaccharide and/or binding partners. Although certain portions of the molecule may not directly participate in this association with a oligosaccharide and/or its binding partners, those portions may still influence the overall conformation of the molecule. This, in turn, may have a significant impact on binding affinities, therapeutic efficacy, drug-like qualities, and potency. Such conformational requirements include the overall three-dimensional structure and orientation of the chemical entity or molecule in relation to all or a portion of the active site or other region of the oligosaccharide and/or binding partners, or the spacing between functional groups of a molecule comprising several chemical entities that directly interact with the oligosaccharide and/or binding partners.

The potential, predicted, inhibitory or binding effect of a molecule on oligosaccharide and/or binding partners may be analyzed prior to its actual synthesis and testing by the use of computer modeling techniques. If the theoretical structure of the given molecule suggests insufficient interaction and association between it and an oligosaccharide and/or binding partners, synthesis and testing of the molecule is obviated. However, if computer modeling indicates a strong interaction, the molecule may then be synthesized and tested for its ability to interact with the oligosaccharide and/or binding partners and inhibit or enhance binding. In this manner, synthesis of inoperative molecules may be avoided. In some cases, inactive molecules are synthesized predicted on modeling and then tested to develop a SAR (structure-activity relationship) for molecules interacting with a specific region of the oligosaccharide and/or binding partners. As used herein, the term "SAR", shall collectively refer to the structure-activity/structure property relationships pertaining to the relationship(s) between a compound's activity/properties and its chemical structure.

One skilled in the art may use one of several methods to identify chemical moieties or entities, compounds, or other agents for their ability to associate with a preselected target site within an oligosaccharide and/or binding partner. In one embodiment, compound design uses computer modeling programs which calculate how different molecules interact with the various sites of the oligosaccharide and/or binding partner, or a fragment thereof. Selected chemical moieties or entities, compounds, or agents may then be positioned in a variety of orientations, or docked, within at least a portion of the target site of an oligosaccharide and/or binding partner(s). Databases of chemical structures are available from, for example, Cambridge Crystallographic Data Center (Cambridge, U.K.) and Chemical Abstracts Service (Columbus, Ohio). Docking may be accomplished using software such as Cerius, Quanta or Sybyl, followed by energy minimization and molecular dynamics with standard molecular mechanics forcefields, such as OPLS-AA, CHARMM or AMBER.

Specialized computer programs may also assist in the process of selecting chemical entities. These include, but are not limited to:

(1) GRID (Goodford, P. J., "A Computational Procedure for Determining Energetically Favorable Binding Sites on Biologically Important Macromolecules" (1985) *J. Med. Chem.* 28, 849-857). Software such as GRID, a program that determines probable interaction sites between probes with various functional group characteristics and the macromolecular surface, can be used to analyze the surface sites to determine structures of similar inhibiting proteins or molecules. The GRID calculations, with suitable inhibiting groups on molecules (e.g., protonated primary amines) as the probe, are used to identify potential hotspots around accessible positions at suitable energy contour levels. GRID is available from Oxford University, Oxford, UK.

(2) MCSS (Miranker, A. and M. Karplus (1991) "Functionality Maps of Binding Sites: A Multiple Copy Simultaneous Search Method." *Proteins: Structure, Function and Genetics* 11: 29-34). MCSS is available from Molecular Simulations, Burlington, Mass.

(3) AUTODOCK (Goodsell, D. S, and A. J. Olsen (1990) "Automated Docking of Substrates to Proteins by Simulated Annealing" *Proteins: Structure, Function, and Genetics* 8: 195-202). AUTODOCK is available from Scripps Research Institute, La Jolla, Calif.

(4) DOCK (Kuntz, I. D. et al. (1982) "A Geometric Approach to Macromolecule-Ligand Interactions" *J. Mol. Biol.* 161: 269-288). The program DOCK may be used to analyze an active site or ligand binding site and suggest ligands with complementary steric properties. DOCK is available from University of California, San Francisco, Calif.

(5) ALADDIN (Van Drie et al. (1989) "ALADDIN: An Integrated Tool of Computer Assisted Molecular Design and Pharmacophore Recognition From Geometric, Steric and Substructure Searching of Three-Dimensional Structures" *J. Comp-Aided Mol. Des.* 3: 225).

(6) CLIX (Davie and Lawrence (1992) "CLIX: A Search Algorithm for Funding Novel Ligands Capable of Binding Proteins of Known Three-Dimensional Structure" *Proteins* 12: 31-41).

(7) GROUPBUILD (Rotstein and Murcko (1993) "Group-Build: A Fragment-Based Method for De Novo Drug Design" *J. Med. Chem.* 36: 1700).

(8) GROW (Moon and Howe (1991) "Computer Design of Bioactive Molecules: A Method for Receptor-Based De Novo Ligand Design" *Proteins* 11: 314).

The molecule of interest may be designed as a whole using either an empty active site or optionally including some portion or portions of a known inhibitor or inhibitors. Software that implements these methods include:

(1) LUDI (Bohm, H.-J. (1992) "The Computer Program LUDI: A New Method for the De Novo Design of Enzyme Inhibitors" *J. Comp. Aid. Molec. Design* 6: 61-78). The program LUDI can determine a list of interaction sites into which to place both hydrogen bonding and hydrophobic fragments. LUDI then uses a library of approximately 600 linkers to connect up to four different interaction sites into fragments. Then smaller "bridging" groups such as —$CH_2$— and —COO— are used to connect these fragments. For example, for the enzyme DHFR, the placements of key functional groups in the well-known inhibitor methotrexate were reproduced by LUDI. See also, Rotstein and Murcko, (1992) *J. Med. Chem.* 36:1700-1710. LUDI is available from Biosym Technologies, San Diego, Calif.

(2) LEGEND (Nishibata, Y. and A. Itai (1991) *Tetrahedron* 47, 8985). LEGEND is available from Molecular Simulations, Burlington, Mass.

(3) LeapFrog (available from Tripos Associates, St. Louis, Mo.).

(4) Aladdin (available from Daylight Chemical Information Systems, Irvine, Calif.)

Other molecular modeling techniques may also be employed in accordance with this invention. See, e.g., Cohen, N. C. et al. (1990) "Molecular Modeling Software and Methods for Medicinal Chemistry, *J. Med. Chem.* 33: 883-894. See also, Navia, M. A. and M. A. Murcko (1992) "The Use of Structural Information in Drug Design", *Current Opinions in Structural Biology* 2: 202-210; and Jorgensen (1998) "BOSS—Biochemical and Organic Simulation System" in the *Encyclopedia of Computational Chemistry* (P. V. R. Schleyer, ed.) Wiley & Sonstra., Athens, U.S.A. 5: 3281-3285).

It is contemplated that during modeling, it may be possible to introduce into the molecule of interest, chemical moieties that may be beneficial for a molecule that is to be administered as a pharmaceutical. For example, it may be possible to introduce into or omit from the molecule of interest, chemical moieties that may not directly affect binding of the molecule to the target area but which contribute, for example, to the overall solubility of the molecule in a pharmaceutically acceptable carrier, the bioavailability of the molecule and/or the toxicity of the molecule. Considerations and methods for optimizing the pharmacology of the molecules of interest can be found, for example, in "Goodman and Gilman's The Pharmacological Basis of Therapeutics" Eighth Edition (Goodman, Gilman, Rall, Nies, & Taylor (eds.)). Pergaman Press (1985); Jorgensen & Duffy (2000) *Bioorg. Med. Chem. Lett.* 10: 1155-1158.

Furthermore, the computer program "Qik Prop" can be used to provide rapid predictions for physically significant descriptions and pharmaceutically-relevant properties of an organic molecule of interest. A 'Rule of Five' probability scheme can be used to estimate oral absorption of the newly synthesized compounds (Lipinski et al. (1997) *Adv. Drug Deliv. Rev.* 23:3).

Programs suitable for pharmacophore selection and design include:
(1) DISCO (Abbot Laboratories, Abbot Park, Ill.);
(2) Catalyst (Bio-CAD Corp., Mountain View, Calif.); and
(3) Chem DBS-3D (Chemical Design Ltd., Oxford, U.K.).

Furthermore, the skilled artisan may use the information available on how to design suitable therapeutically active and pharmaceutically useful compounds, and use this information in the design of inhibitors or enhancers of the invention. See, for example, Lipinski et al. (1997) *Ad. Drug Deliv. Reviews* 23: 3-25; Van de Waterbeemd et al. (1996) *Quantitative Structure-Activity Relationships* 15: 480-490; and Cruciani et al. (2000), *Theochem-J. Mol. Struct.* 503: 17-30.

The entry of the sequences of the oligosaccharide and/or binding partner binding sites into the computer programs discussed above results in the calculation of most probable structure of the macromolecule. These structures can be combined and refined by additional calculations using such programs to determine the probable or actual three-dimensional structure of the oligosaccharide and/or binding partners, including potential or actual active or binding sites of ligands.

Instead of designing molecules of interest entirely de novo it is contemplated that pre-existing molecules, oligosaccharides, or proteins thereof may be used as a starting point for the design of a new candidate. It is contemplated that many of the approaches useful for designing molecules de novo may also be useful for modifying existing molecules.

It is contemplated that knowledge of the spatial relationship between an inhibitor or enhancer of binding between an oligosaccharide and/or binding partners, and its respective binding site within an oligosaccharide and/or binding partner, permits the design of modified inhibitors or enhancers that may have better binding properties, for example, higher binding affinity and/or specificity, relative to the molecule from which it was derived. Alternatively, knowledge of inhibitor contact sites within an oligosaccharide and/or binding partners permits the synthesis of a new molecule that contain, for example, a portion of a first molecule that binds to the contact site and another portion that contributes additional functionality.

It is contemplated that a variety of modified molecules may be designed. For example, it is contemplated that by knowing the spatial relationship of one or more inhibitors relative to the oligosaccharide and/or binding partners it is possible to generate new inhibitors. Accordingly, from this information the skilled artisan may not only identify contact locations within the oligosaccharide and/or binding partner that can be used for de novo drug design, as discussed above, but also may identify portions of an inhibitor that can act as an oligosaccharide and/or binding partner binding domain.

Based on the information provided herein, the skilled artisan may readily identify and produce hybrid inhibitors or enhancers that comprise an oligosaccharide and/or binding partner binding domain and an oligosaccharide and/or binding partner binding domain of a second, different enhancer or inhibitor. The resulting hybrid inhibitors or enhancers preferably bind to each of respective contact locations within the oligosaccharide and/or binding partner(s) simultaneously. It is contemplated that the skilled artisan may produce a hybrid inhibitor or enhancer that binds to an oligosaccharide and/or binding partner(s) with a higher affinity and/or have higher inhibitory or enhancing activity than either of the individual template inhibitors or enhancers used to generate the hybrid.

Furthermore, the invention provided herein permits the skilled artisan to use the information pertaining to the identification of an oligosaccharide and/or binding partner domain and to design other types of inhibitors or enhancers. For example, with an understanding of the oligosaccharide and/or binding partner contact region and the surrounding environment, the skilled artisan can provide novel molecules, a portion of which is based upon the oligosaccharide binding region (binding domain) and another portion of which (effector domain) can be designed as a novel space filling domain that sterically inhibits or disrupts or alternatively enhances oligosaccharide and/or binding partner binding. For example, the skilled artisan may combine the oligosaccharide with, for example, a novel chemical moiety. However, it is contemplated that the skilled artisan may take advantage of one or more of the many of the oligosaccharide or binding partner contact regions disclosed herein to design entirely new binding and effector domains.

Furthermore, the present invention permits the skilled artisan to design molecules, for example, selective oligosaccharide-binding partners inhibitors or enhancers that are tailored to be more potent with respect to the oligosaccharide and/or binding partner. Also, the invention permits the skilled artisan to design modifications to starting compounds, such as an inhibitor, that will bind more tightly to a target and less tightly to a non-targeted oligosaccharide and/or binding partner.

Once a candidate molecule has been designed or selected by the above methods, the affinity with which that molecule may bind to the oligosaccharide and/or binding partners may be tested and optimized by computational evaluation and/or by testing biological activity after synthesizing the compound. Candidate molecules may interact with the oligosaccharide and/or binding partner in more than one conformation each of which has a similar overall binding energy. In those cases, the deformation energy of binding may be considered to be the difference between the energy of the free molecule and the average energy of the conformations observed when the molecule binds to oligosaccharide and/or binding partner.

A molecule designed or selected as binding to an oligosaccharide and/or binding partner may be further computationally optimized so that in its bound state it preferably lacks repulsive electrostatic interaction with the target region. Such non-complementary (e.g., electrostatic) interactions include repulsive charge-charge, dipole-dipole and charge-dipole interactions. Specifically, the sum of all electrostatic interactions between the inhibitor and the enzyme when the inhibitor is bound to the oligosaccharide and/or binding partner, preferably make a neutral or favorable contribution to the enthalpy of binding. Weak binding compounds can also be designed by these methods so as to determine SAR.

Specific computer programs that can evaluate a compound deformation energy and electrostatic interaction are available in the art. Examples of suitable programs include: Gaussian 92, revision C (M. J. Frisch, Gaussian, Inc., Pittsburgh, Pa.); AMBER, version 4.0 (P. A. Kollman, University of California at San Francisco, Calif.); QUANTA/CHARMM (Molecular Simulations, Inc., Burlington, Mass.); OPLS-AA ("OPLS Force Fields." W. L. Jorgensen. Encyclopedia of Computational Chemistry, Schleyer, Ed.; Wiley: New York, 1998; Vol. 3, pp 1986-1989.) and Insight II/Discover (Biosysm Technologies Inc., San Diego, Calif.). These programs may be implemented, for instance, using a Silicon Graphics workstation, IRIS 4D/35 or IBM RISC/6000 workstation model 550. Other hardware systems and software packages are known to those skilled in the art.

Once a molecule of interest has been selected or designed, as described above, substitutions may then be made in some of its atoms or side groups in order to improve or modify its binding properties. Generally, initial substitutions are conservative, i.e., the replacement group will approximate the same size, shape, hydrophobicity and charge as the original group. It should, of course, be understood that components known in the art to alter conformation should be avoided. Such substituted chemical compounds may then be analyzed for efficiency of fit to the oligosaccharide and/or binding partner by the same computer methods described in detail, above.

A lead molecule of the present invention can be, but is not limited to, at least one selected from a lipid, nucleic acid, peptide, small organic or inorganic molecule, chemical compound, element, saccharide, isotope, carbohydrate, imaging agent, lipoprotein, glycoprotein, enzyme, analytical probe, and an antibody or fragment thereof, any combination of any of the foregoing, and any chemical modification or variant of any of the foregoing. In addition, a lead molecule may optionally comprise a detectable label. Such labels include, but are not limited to, enzymatic labels, radioisotope or radioactive compounds or elements, fluorescent compounds or metals, chemiluminescent compounds and bioluminescent compounds. Well known methods may be used for attaching such a detectable label to a lead molecule.

Methods useful for synthesizing lead molecules such as lipids, nucleic acids, peptides, small organic or inorganic molecules, chemical compounds, elements, saccharides, isotopes, carbohydrates, imaging agents, lipoproteins, glycoproteins, enzymes, analytical probes, antibodies, and antibody fragments are well known in the art. Such methods include the traditional approach of synthesizing one such lead molecule, such as a single defined peptide, at a time, as well as combined synthesis of multiple lead molecules in a one or more containers. Such multiple lead molecules may include one or more variants of a previously identified lead molecule. Methods for combined synthesis of multiple lead molecules are particularly useful in preparing combinatorial libraries, which may be used in screening techniques known in the art.

By way of example, it is well known in the art that multiple peptides and oligonucleotides may be simultaneously synthesized. Lead molecules that are small peptides up to 50 amino acids in length, may be synthesized using standard solid-phase peptide synthesis procedures, for example, procedures similar to those described in Merrifield (1963) *J. Am. Chem. Soc.*, 85: 2149.

It is contemplated that a synthetic peptide in accordance with the invention may comprise naturally occurring amino acids, unnatural amino acids, and/or amino acids having specific characteristics, such as, for example, amino acids that are positively charged, negatively charged, hydrophobic, hydrophilic, or aromatic. As used herein, the term "naturally occurring amino acids" refers to the L-isomers of amino acids normally found in proteins. The predominant naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, and lysine. Unless specifically indicated, all amino acids are referred to in this application are in the L-form. Furthermore, as used herein, the term "unnatural amino acids" refers to amino acids that are not naturally found in proteins. For example, selenomethionine.

Amino acids that are "positively charged" include any amino acid having a positively charged side chain under normal physiological conditions. Examples of positively charged naturally occurring amino acids include, for example, arginine, lysine, and histidine. Conversely, amino acids that are "negatively charged" include any amino acid having a negatively charged side chains under normal physiological conditions. Examples of negatively charged naturally occurring amino acids include, for example, aspartic acid and glutamic acid.

As used herein, the term "hydrophobic amino acid" includes any amino acids having an uncharged, nonpolar side chain that is relatively insoluble in water. Examples of naturally occurring hydrophobic amino acids include, for example, alanine, leucine, isoleucine, valine, proline, phenylalanine, tryptophan, and methionine. In addition, as used herein, the term "hydrophilic amino acid" refers to any amino acids having an uncharged, polar side chain that is relatively soluble in water. Examples of naturally occurring hydrophilic amino acids include, for example, serine, threonine, tyrosine, asparagine, glutamine and cysteine.

Finally, as used herein, the term "aromatic" refers to amino acid residues which side chains have delocalized conjugated system. Examples of aromatic residues include, for example, phenylalanine, tryptophan, and tyrosine.

With regard to the production of non-peptide small organic molecules which act as a ligand in the present invention, these molecules can be synthesized using standard organic chemistries well known and thoroughly documented in the patent and other literatures.

Many of the known methods useful in synthesizing lead of the present invention may be automated, or may otherwise be practiced on a commercial scale. As such, once a lead molecule has been identified as having commercial potential, mass quantities of that molecule may easily be produced.

Molecules designed, selected and/or optimized by methods described above, once produced, may be characterized using a variety of assays known to those skilled in the art to determine whether the compounds have biological activity. For example, the molecules may be characterized by conventional assays, including but not limited to those assays described below, to determine whether they have a predicted activity, binding activity and/or binding specificity.

Furthermore, high-throughput screening may be used to speed up analysis using such assays. As a result, it may be possible to rapidly screen new molecules for their ability to interact with oligosaccharide and/or binding partner using the tools and methods of the present invention. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

(1) Surface Binding Studies. A variety of binding assays may be useful in screening new molecules for their binding activity. One approach includes surface plasmon resonance (SPR) which can be used to evaluate the binding properties molecules of interest with respect to an oligosaccharide and/or binding partner or a fragment thereof.

SPR methodologies measure the interaction between two or more macromolecules in real-time through the generation of a quantum-mechanical surface plasmon. This system permits rapid and sensitive real-time measurement of the molecular interactions without the need to label either component.

(2) Immunodiagnostics and Immunoassays. These are a group of techniques that can be used for the measurement of specific biochemical substances, commonly at low concentrations in complex mixtures such as biological fluids, that depend upon the specificity and high affinity shown by suitably prepared and selected antibodies for their complementary antigens. A substance to be measured must, of necessity, be antigenic—either an immunogenic macromolecule or a haptenic small molecule. To each sample a known, limited amount of specific antibody is added and the fraction of the antigen combining with it, often expressed as the bound:free ratio, is estimated, using as indicator a form of the antigen labeled with radioisotope (radioimmunoassay), fluorescent molecule (fluoroimmunoassay), stable free radical (spin immunoassay), enzyme (enzyme immunoassay), or other readily distinguishable label.

Antibodies can be labeled in various ways, including: enzyme-linked immunosorbent assay (ELISA); radioimmuno assay (RIA); fluorescent immunoassay (FIA); chemiluminescent immunoassay (CLIA); and labeling the antibody with colloidal gold particles (immunogold).

Common assay formats include the sandwich assay, competitive or competition assay, latex agglutination assay, homogeneous assay, microtitre plate format and the microparticle-based assay.

(3) Enzyme-linked immunosorbent assay (ELISA). ELISA is an immunochemical technique that avoids the hazards of radiochemicals and the expense of fluorescence detection systems. Instead, the assay uses enzymes as indicators. ELISA is a form of quantitative immunoassay based on the use of antibodies (or antigens) that are linked to an insoluble carrier surface, which is then used to "capture" the relevant antigen (or antibody) in the test solution. The antigen-antibody complex is then detected by measuring the activity of an appropriate enzyme that had previously been covalently attached to the antigen (or antibody).

General methods and compositions for practicing ELISA are described, for example, in Crowther (1995) *ELISA—Theory and Practice (Methods in Molecular Biology)*, Humana Press; Challacombe and Kemeny, (1998) *ELISA and Other Solid Phase Immunoassays—Theoretical and Practical Aspects*, John Wiley; Kemeny, (1991) *A Practical Guide to ELISA*, Pergamon Press; Ishikawa, (1991) *Ultrasensitive and Rapid Enzyme Immunoassay* (Laboratory Techniques in Biochemistry and Molecular Biology) Elsevier.

(4) Colorimetric Assays. Colorimetry is any method of quantitative chemical analysis in which the concentration or amount of a compound is determined by comparing the color produced by the reaction of a reagent with both standard and test amounts of the compound, often using a colorimeter. A colorimeter is a device for measuring color intensity or differences in color intensity, either visually or photoelectrically.

Standard colorimetric assays of beta-galactosidase enzymatic activity are well known to those skilled in the art (see, for example, Norton et al. (1985) *Mol. Cell. Biol.* 5: 281-290). A colorimetric assay can be performed on whole cell lysates using O-nitrophenyl-β-D-galactopyranoside (ONPG, Sigma) as the substrate in a standard colorimetric beta-galactosidase assay (Sambrook et al. (1989) *Molecular Cloning—A Laboratory Manual*, Cold Spring Harbor Laboratory Press). Automated colorimetric assays are also available for the detection of β-galactosidase activity, as described in U.S. Pat. No. 5,733,720.

(5) Immunofluorescence Assays. Immunofluorescence or immunofluorescence microscopy is a technique in which an antigen or antibody is made fluorescent by conjugation to a fluorescent dye and then allowed to react with the complementary antibody or antigen in a tissue section or smear. The location of the antigen or antibody can then be determined by observing the fluorescence by microscopy under ultraviolet light.

A general description of immunofluorescent techniques appears for example, in Knapp et al. (1978) *Immunofluorescence and Related Staining Techniques*, Elsevier; Allan, (1999) *Protein Localization by Fluorescent Microscopy—A Practical Approach* (The Practical Approach Series) Oxford University Press; Caul, (1993) *Immunofluorescence Antigen Detection Techniques in Diagnostic Microbiology*, Cambridge University Press. For detailed explanations of immunofluorescent techniques applicable to the present invention, see, for example, U.S. Pat. Nos. 5,912,176; 5,869,264; 5,866,319; and 5,861,259.

(6) Fluorescence Polarization. Fluorescence polarization (FP) is a measurement technique that can readily be applied to protein-protein and protein-ligand interactions in order to derive $IC_{50}$s and Kds of the association reaction between two molecules. In this technique one of the molecules of interest is conjugated with a fluorophore. This is generally the smaller molecule in the system (in this case, the molecule of interest). The sample mixture, containing both the ligand-probe conjugate and the oligosaccharide and/or binding partner or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(7) Protein Synthesis. It is contemplated that, in addition to characterization by the foregoing biochemical assays, the molecule of interest may also be characterized as a modulator (for example, an inducer of protein synthesis or an inhibitor of protein synthesis) of the functional activity of the oligosaccharide and/or binding partner.

Inhibitors of protein synthesis may be assayed on the cellular level. For example, molecules of interest can be assayed for inhibitory action against organisms, for example, microorganism, by growing the micro-organism of interest in media either containing or lacking the molecule of interest. Growth inhibition may be indicative that the molecule may be acting as a protein synthesis inhibitor or by inhibiting binding or the microorganism to a receptor.

Furthermore, more specific protein synthesis inhibition assays may be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3H$ leucine or $^{35}S$ methionine, or similar experiments can be performed to investigate protein synthesis activity.

An increase in the amount or the rate of protein synthesis in the cell in the presence of a molecule of interest indicates that the molecule is an inducer of protein synthesis. A decrease in the rate or the amount of protein synthesis indicates that the molecule is a inhibitor of protein synthesis.

It is contemplated that once identified, the active molecules of the invention may be incorporated into any suitable carrier prior to use. More specifically, the dose of active molecule, mode of administration and use of suitable carrier will depend upon the target and non-target organism of interest.

The present invention provides for both prophylactic and therapeutic methods of treating a subject having a disease or condition associated with abnormal oligosaccharide—binding partner binding. Subjects at risk for such a disease can be identified by a diagnostic or prognostic assay, e.g., as described herein. Administration of a prophylactic agent can occur prior to the manifestation of symptoms characteristic of abnormal oligosaccharide-binding partner binding, e.g., such that development of the disease associated with abnormal oligosaccharides-binding partners binding is prevented or, alternatively, delayed in its progression. In general, the prophylactic or therapeutic methods comprise administering to the subject an effective amount of a compound which is capable of agonizing a wild-type oligosaccharide-binding partner binding or antagonizing a mutant (defective) oligosaccharide-binding partner binding. Examples of suitable compounds include the antagonists, agonists or mimics described in detail herein.

Toxicity and therapeutic efficacy of such compounds can be determined by standard pharmaceutical procedures in cell cultures or experimental animals, e.g., for determining the $Ld_{50}$ (the dose lethal to 50% of the population) and the $Ed_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It is contemplated that with regard to mammalian recipients, the compounds of interest may be administered by any conventional approach known and/or used in the art. Thus, as appropriate, administration can be oral or parenteral, including intravenous and intraperitoneal routes of administration. In addition, administration can be by periodic injections of a bolus, or can be made more continuous by intravenous or intraperitoneal administration from a reservoir which is external (e.g., an intravenous bag). Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. In certain embodiments, the compounds of the invention can be therapeutic-grade. That is, certain embodiments comply with standards of purity and quality control required for administration to humans. Veterinary applications are also within the intended meaning as used herein.

The formulations, both for veterinary and for human medical use, of the drugs according to the present invention typically include such drugs in association with a pharmaceutically acceptable carrier therefore and optionally other therapeutic ingredient(s). The carrier(s) should be "acceptable" in the sense of being compatible with the other ingredients of the formulations and not deleterious to the recipient thereof. Pharmaceutically acceptable carriers, in this regard, are intended to include any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations may conveniently be presented in dosage unit form and may be prepared by any of the methods well known in the art of pharmacy/microbiology. In general, some formulations are prepared by bringing the drug into association with a liquid carrier or a finely divided solid carrier or both, and then, if necessary, shaping the product into the desired formulation.

A pharmaceutical composition of the invention should be formulated to be compatible with its intended route of administration. Examples of routes of administration include oral or parenteral, e.g., intravenous, intraarterial, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's *Pharmaceutical Sciences*, (Gennaro, A., ed.), Mack Pub., (1990). Formulations for parenteral administration can also include glycocholate for buccal administration, methoxysalicylate for rectal administration, or cutric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, hydrogenated naphthalenes, and the like. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration may be in the form of discrete units such as capsules, gelatin capsules, sachets, tablets, troches, or lozenges, each containing a predetermined amount of the drug; in the form of a powder or granules; in the form of a solution or a suspension in an aqueous liquid or non-aqueous liquid; or in the form of an oil-in-water emulsion or a water-in-oil emulsion. The drug may also be administered in the form of a bolus, electuary or paste. A tablet may be made by compressing or moulding the drug optionally with one or more accessory ingredients. Compressed tablets may be prepared by compressing, in a suitable machine, the drug in a free-flowing form such as a powder or granules, optionally mixed by a binder, lubricant, inert diluent, surface active or dispersing agent. Moulded tablets may be made by moulding, in a suitable machine, a mixture of the powdered drug and suitable carrier moistened with an inert liquid diluent.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Formulations suitable for topical administration, including eye treatment, include liquid or semi-liquid preparations such as liniments, lotions, gels, applicants, oil-in-water or water-in-oil emulsions such as creams, ointments or pasts; or solutions or suspensions such as drops. Formulations for topical administration to the skin surface can be prepared by dispersing the drug with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect may be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents, bile salts, and filsidic acid derivatives. In addition, detergents may be used to facilitate permeation. Transmucosal administration can be accomplished through the use of nasal sprays or suppositories. For transdermal administration, the active compounds typically are formulated into ointments, salves, gels, or creams as generally known in the art. A wash solution can be used locally to treat an injury or inflammation to accelerate healing.

The active compounds may be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials also can be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811. Microsomes and microparticles also can be used.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres, which offer the possibility of local noninvasive delivery of drugs over an extended period of time. This technology utilizes microspheres of precapillary size that can be injected via a coronary catheter into any selected part of the body, e.g., the eye, or other organs without causing inflammation or ischemia. The administered therapeutic is slowly released from these microspheres and taken up by surrounding tissue cells (e.g. endothelial cells).

Where the active compound is to be used as part of a transplant procedure, it can be provided to the living tissue or organ to be transplanted prior to removal of tissue or organ from the donor. The drug can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art.

Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

The effective concentration of the compounds to be delivered in a therapeutic composition will vary depending upon a number of factors, including the final desired dosage of the compound to be administered and the route of administration. The preferred dosage to be administered also is likely to depend on such variables as the type and extent of disease or indication to be treated, the overall health status of the particular patient, the relative biological efficacy of the compound delivered, the formulation of the drug, the presence and types of excipients in the formulation, and the route of administration. In general terms, the drugs of this invention can be provided to an individual using typical dose units deduced from the earlier-described mammalian studies using non-human primates and rodents.

Active compound identified or designed by a method of the invention also include precursors of the active compounds. The term precursors refers to a pharmacologically inactive (or partially inactive) derivative of a parent molecule that requires biotransformation, either spontaneous or enzymatic, within the organism to release the active compounds. Precursors are variations or derivatives of the compounds of the invention which have groups cleavable under metabolic conditions. Precursors become the active compounds of the invention which are pharmaceutically active in vivo, when they undergo solvolysis under physiological conditions or undergo enzymatic degradation. Precursor forms often offer advantages of solubility, tissue compatibility, or delayed release in the mammalian organism (see Bundgard, *Design of Prodrugs*, pp. 7-9, 21-24, Elsevier, Amsterdam (1985); and Silverman, *The Organic Chemistry of Drug Design and Drug Action*, pp. 352-401, Academic Press, San Diego, Calif. (1992).

Active compound as identified or designed by the methods described herein can be administered to individuals to treat disorders (prophylactically or therapeutically). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a drug as well as tailoring the dosage and/or therapeutic regimen of treatment with the drug.

With regard to mammals, it is contemplated that the effective dose of a protein synthesis inducer or inhibitor will be in the range of about 0.01 to about 50 mg/kg, preferably about 0.1 to about 10 mg/kg of body weight, administered in single or multiple doses. Typically, the inducer or inhibitor may be administered to a human recipient in need of treatment at a daily dose range of about 1 to about 2000 mg per patient.

The oligosaccharide-binding partner therapeutic may be administered alone or in combination with other molecules known to have a beneficial effect on oligosaccharide-binding partner, including molecules capable of tissue repair and regeneration and/or inhibiting inflammation. Examples of useful cofactors include basic fibroblast growth factor (bFGF), ciliary neurotrophic factor (CNTF), axokine (a mutein of CNTF), leukemia inhibitory factor (LIF), neurotrophin 3 (NT-3), neurotrophin-4 (NT-4), nerve growth factor (NGF), insulin-like growth factor II, prostaglandin E2, 30 kD survival factor, taurine, and vitamin A. Other useful cofactors include symptom-alleviating cofactors, including antiseptics, antibiotics, antiviral and antifungal agents and analgesics and anesthetics.

The oligosaccharide-binding partner therapeutics also may be associated with means for targeting the oligosaccharide-binding partner therapeutics to a desired tissue. Alternatively, an antibody or other binding protein that interacts specifically with a surface molecule on the desired target tissue cells also may be used. Such targeting molecules further may be covalently associated to the oligosaccharide-binding partner therapeutic, e.g., by chemical crosslinking, or by using standard genetic engineering means to create, for example, an acid labile bond such as an Asp-Pro linkage. Useful targeting molecules may be designed, for example, using the simple chain binding site technology disclosed, for example, in U.S. Pat. No. 5,091,513.

The present invention is further illustrated by the following examples, which should not be construed as limiting in any way. The contents of all cited references (including literature references, issued patents, published patent applications as cited throughout this application) are hereby expressly incorporated by reference.

The practice of the present invention can employ, unless otherwise indicated, conventional techniques of cell biology, cell culture, molecular biology, transgenic biology, microbiology, recombinant DNA, and immunology, which are within the skill of the art. Such techniques are explained fully in the literature.

Practice of the invention will be still more fully understood from the following examples, which are presented herein for illustration only and should not be construed as limiting the invention in any way. Variations and alternate embodiments will be apparent to those of skill in the art. The contents of all cited references (including literature references, issued patents, and published patent applications that may be cited throughout this application) are hereby expressly incorporated by reference. The practice of the present invention will employ, unless otherwise indicated, conventional techniques of molecular biology and protein chemistry, which are within the skill of the art.

EXAMPLES

Example 1

Labeling and Gel Mobility Shift Assay with Pentasaccharide Sulfated at Various Positions The oligosaccharide heparin is a heavily sulfated at 2-O, 6-O and N positions, and is exclusively located in mast cells (Rosenberg (2001) New Engl. J. Med. 344: 673-5). Heparan sulfate (HS) is typically less extensively sulfated than heparin and is widely distributed in all animal tissues. Along the HS chain, the majority of N-sulfated glucosamine residues and various types of O-sulfated residues are clustered in a series of short functional domains separated by relatively less sulfated oligosaccharide sequences (Gallagher (2001) J. Clin. Invest. 108: 357-361). Because heparin shares a very high degree of structural similarity with these HS domains and is available in abundant quantity, it is widely used for functional studies of HS. Extensive heterogeneity, including the length of the chain, the extent of sulfation and the core carbohydrate sequence, occurs in HS. It is very likely that this heterogeneity is utilized for the carbohydrate sequence-specific binding of particular molecules (Lindahl (1998) supra. With the accumulation of the information concerning the biological roles of HS, its biological functions relate predominantly to their ability to interact with proteins (Elko and Selleck (2002) Ann. Rev. Biochem. 71: 435-471; Lindahl (1998) supra. For instance, they interact with lipoprotein lipase (Parthasarathy et al. (1994) J. Biol. Chem. 269: 22391-22396), antithrombin III (Rosenberg (2001) supra), epidermal growth factor (EGF) (Higashiyama et al. (1993) J. Cell. Biol. 122: 933-940), fibroblast growth factors (FGF) and their receptors (FGFR) (Givol and Yayon (1992) supra; Kan et al. (1993) supra). The interaction of HS with proteins was examined and characterized using the gel mobility shift assay (GMSA), as described below.

Materials

Heparin oligosaccharides were purchased from Iduron (Manchester, UK). 3-O desulfated pentasaccharide was obtained from Dr. P. Sinay (Departement de Chimie, Ecole Normale Superieure, France). The 3-O, 6-O doubly desulfated pentasaccharide was prepared by treating 3-O desulfated pentasaccharide with 6-O sulfatase (Seikagaku America, Falmouth, Mass.) according to standard methods. Antithrombin III (AT-III) was prepared as previously described (Damus and Rosenberg (1976) Methods Enzymol. 45: 653-669). Completely desulfated and N-resulfated heparin sulfate (DSNS) was obtained from Seikagaku America (Falmouth, Mass.). APS kinase was used for making the 3'-phosphoadenosine 5'-phosphosulfate (PAPS) and was obtained from Dr. Irvin Segel (U Cal-Davis, Calif.). Other biochemicals were obtained from Sigma.

All sulfotransferases were cloned and expressed in COS or Baculovirus as previously described (Liu et al. (1999) supra; Zhang et al. (2001a) supra; Shworak et al. (1997) J. Biol. Chem. 272: 28008-28019).

[$^{35}$S] 3'-phosphoadenosine 5'-phosphosulfate (PAPS) treatment of polysaccharides and in vitro modification were performed as previously described (Zhang et al. (2001a) supra; Wu et al. (2002) FASEB J. 16:539-545). Briefly, for a 25 μl reaction, 2 μg of substrate (HS or heparin) and 12.5 μl of 2× buffer (50 mM MES (pH 7.0), 1% (w/v) Triton X-100, 5 mM MnCl$_2$, 5 mM MgCl$_2$, 2.5 mM CaCl$_2$, 0.075 mg/ml protamine chloride, 1.5 mg/ml bovine serum albumin) was combined with 70 ng of sulfotransferase, 2 μl [$^{35}$S]PAPS (~1×10$^7$ cpm), and the appropriate amount of water. The reaction was incubated at 37° C. for 20 minutes and stopped by heating to 75° C. for 3 minutes. The reaction was centrifuged at 10,000 g for 3 minutes and the superantant was used for GMSA.

In order to demonstrate GMSA with an oligosaccharide (e.g., HS) and binding partner protein (e.g., AT-III), the interaction between a short HS pentasaccharide and AT-ITT was examined as a model system. The starting pentasaccharide lacked a 3-O sulfation and a 6-O sulfation, both of which are critical for binding to AT-III (Petitou et al. (1988) Eur. J. Biochem. 176: 637-640). [$^{35}$S] was then added to the pentasaccharide by 3-OST-1 and/or 6-OST-1. The products with [$^{35}$S] at the critical 3-O position only, at the critical 6-O position only and at both the 3-O and 6-O positions were named 3S, 6S, and 3S6S, respectively (FIG. 1A).

The modified pentasaccharides were then subject to a GMSA. Briefly, for a typical 20 μl binding reaction, 10 ng of oligosaccharide (around 10,000 cpm) was mixed with appropriate amount of AT-III in the binding buffer (12% glycerol, 20 mM Tris-HCl (pH 7.9), 100 mM KCl, 1 mM EDTA, and 1 mM DTT). The reaction was incubated at room temperature (23° C.) for 20 minutes. Multiple reactions were usually carried out at the same time. Half of the reaction (10 μl) was then applied to a 4.5% native polyacrylamide gel (with 0.1% bisacrylamide). The gel buffer was 10 mM Tris (pH 7.4) and 1 mM EDTA, and the electrophoresis buffer was 40 mM Tris (pH 8.0), 40 mM acetic acid, 1 mM EDTA. The gel was run under 6 volts/cm for 1 to 2 hours using a SE 250 Mighty Small II gel apparatus (Hoefer Scientific Instruments, San Francisco). After the electrophoresis was finished, the gel was transferred to a 3 MM paper and dried under vacuum.

The dried gel was autoradiographed by a PhosphorImager 445SI (Molecular Dynamics, Sunnyvale, Calif.). The image was analyzed with NIH Image 1.60 and the peak values were collected. The ratio between the bound and free oligosaccharides was then calculated according to the peak values and the concentrations of these oligosaccharides in the binding reaction were derived. The dissociation constant was then calculated on the basis of concentrations of free and bound oligosaccharides and protein.

Figure 1B:
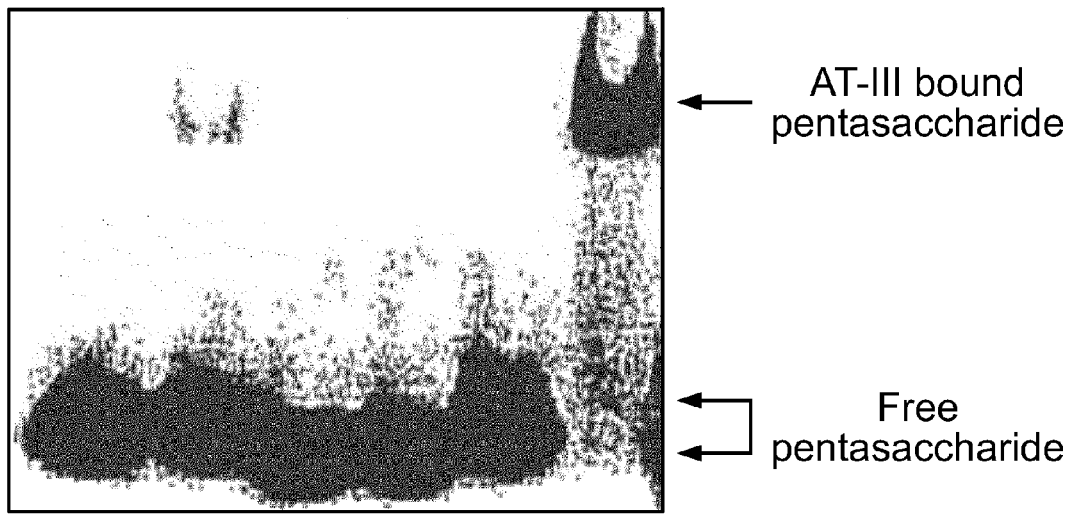
FIG. 1B shows the results of a gel mobility shift assay (GMSA) with the labeled pentasaccharides of FIG. 1A. For each lane, about 100,000 cpm of radiolabeled pentasaccharide was incubated with or without 5 µg of AT-III at room temperature for 20 minutes and the results were resolved by polyacrylamide gel electrophoresis (PAGE) in a 4.5% native gel.

As expected, 6S, which lacked the critical 3-O sulfation, did not bind to AT-III and thus was not shifted (i.e., retarded) by AT-III, but the 3S6S could bind to AT-III and was gel shifted almost completely. On the other hand, 3S, which lacked the critical 6-O sulfation, was very slightly shifted by AT-III (FIG. 1B). After densitometric analysis, the binding affinity Kd=[AT-III]×[pentasaccharide] divided by [AT-III-pentasaccharide] of 3S6S to AT-III was estimated to be about 80 times that of 3S to AT-III. In addition, 3S, 6S, and 3S6S were observed to have different mobilities, indicating that modification of the pentasaccharide affected the charge density and the molecular structure of the oligosaccharide. The results of this experiment demonstrated that 3-O and 6-O sulfates work in a thermodynamically linked fashion to cooperatively increase the binding affinity of the pentasaccharide for AT-III. The experiment also demonstrated that GMSA can be used for studying the interaction between HS and its binding partners.

Example 2

Figure 2A:
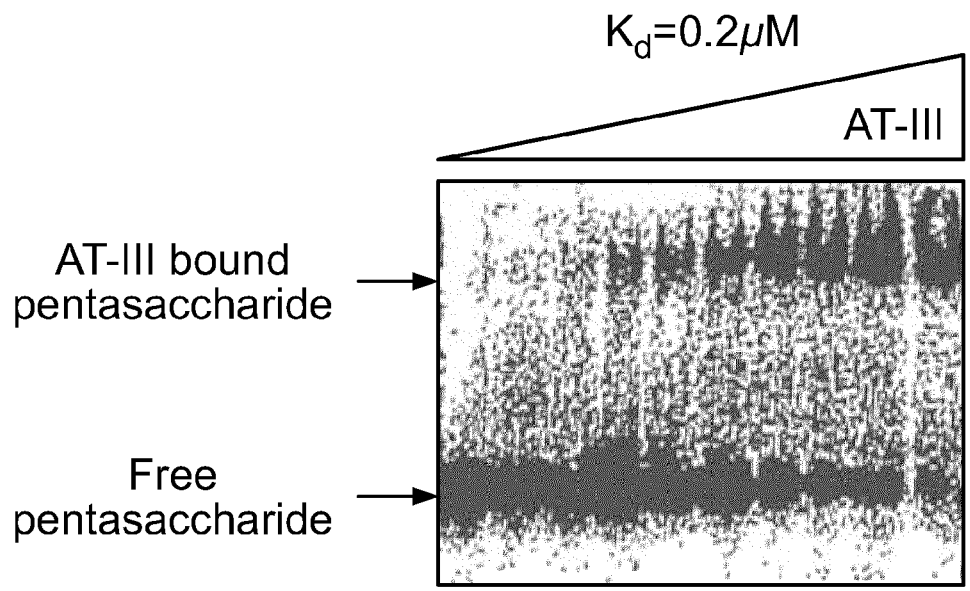
FIG. 2A shows the results of a GMSA measuring the AT-III/pentasaccharide binding constant. Each lane contains 120 ng of radiolabeled pentasaccharide (specific activity $3.3 \times 10^{12}$ cpm/g). From left to right, each lane contained 0, 25, 50, 100, 250, 500, 1000, 2500, 5000 or 10000 ng of AT-III, respectively.
Figure 2B:
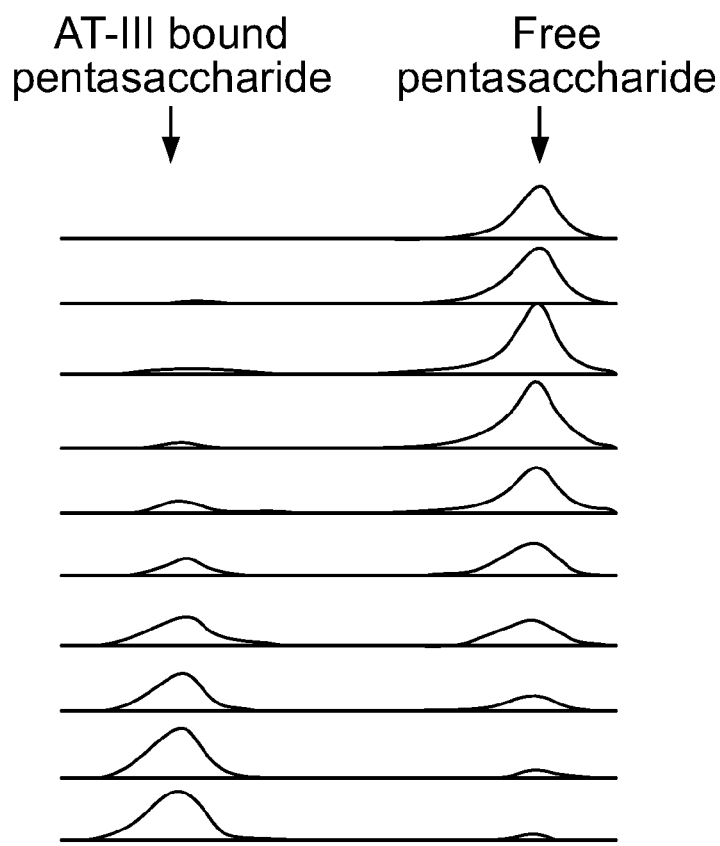
FIG. 2B shows a graphical representation of the results shown in the gel in FIG. 2A, analyzed with an NIH image 1.60 program.

Measurement of the Affinity Between AT-III and the Fully Sulfated HS Pentasaccharide The affinity of HS to proteins is essential for the functions of HS. The affinity between 3S6S (sulfated at both the 3-O and 6-O positions) and AT-III was measured using GMSA. In this experiment, the same amount of 3S6S pentasaccharide (120 ng, with a specific activity of 3.3×10$^6$ cpm/μg) but increasing amount of AT-III (0, 25, 50, 100, 250, 500, 1000, 2500, 5000 and 10000 ng) were combined for each binding reaction as described in Example 1. AT-III bound pentasaccharide was visible at the level of 50 ng of AT-III (less than 1 pmol) (FIG. 2A). The radiogram was analyzed with an NIH Image 1.60 program and the peak values were collected (FIG. 2B). The concentrations of free and bound pentasaccharides were then derived according to standard methods. The dissociation constant K$_d$ was calculated to be 0.16±0.07 μM, which is consistent with the literature (Atha et al. (1985) Biochemistry 24: 6723-6729). Although affinity measurement by electrophoresis for heparin was introduced by Lee and Lander (Lee and Lander (1991) Proc. Natl. Acad. Sci. USA 88: 2768-2772, the instant methods allow for the study of functional features on HS.

Example 3

Minimum Length and the Effect of Length of Heparin on AT-III Binding

Figure 3:
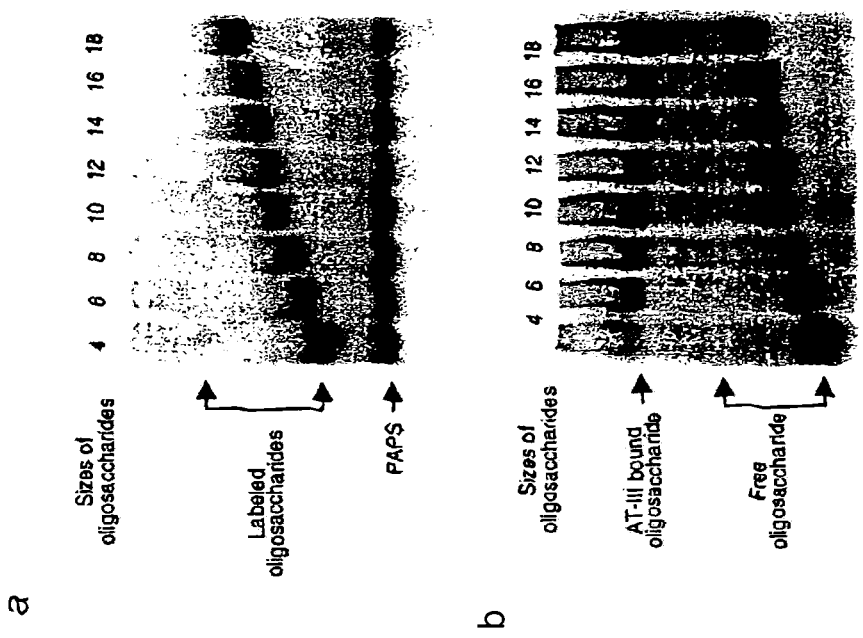
FIG. 3A shows the results of a GMSA demonstrating the minimum oligosaccharide length required for AT-III binding. An oligosaccharide ladder was radiolabeled using 3-OST-1 and separated by PAGE on a 15% gel.
FIG. 3B shows the results of a GMSA in which the oligosaccharides of the labeled ladder in FIG. 3A were incubated with AT-III.

Information on the minimal binding oligosaccharides such as IIS is vital for understanding the rules of oligosaccharide-binding partner (e.g., HS-protein) interaction and for the design of mimics that can specifically target the binding sites for oligosaccharides on binding partners and/or the binding sites for binding partners on oligosaccharides to treat human diseases. As an illustration, the minimal binding length of AT-III for oligosaccharides was determined. To do this, an oligosaccharide ladder from hexasaccharide to octadecasaccharide was radiolabeled with [$^{35}$S] using 3-OST-1 (FIG. 3A) as described above in Example 1. The oligosaccharides in this experiment were already 3-O and 6-O sulfated. The probes were incubated with 5 μg AT-III and separated on a 4.5% native PAGE gel. The binding between the oligosaccharides and AT-III was shown as the shifted bands (FIG. 3B). While significant amount of hexasaccharide and larger oligosaccharides could be shifted by AT-III, tetrasaccharide was not shifted (FIG. 3B). Considering that the pentamer 3S6S bound to AT-III strongly (FIG. 1B), it appears that the minimal length for AT-III binding was a pentasaccharide. It appeared that increasing the size of the oligosaccharide resulted in more binding, perhaps because an AT-III binding site is more likely to be intact in a long oligosaccharide than in a short one.

Example 4

A Specific Fraction of Oligosaccharides Binds to AT-III

When studying the interaction(s) between a heterogenously modified oligosaccharide, such as e.g., HS, and a binding partner (e.g., protein), it is very important to know if the interaction is sequence specific (Gallagher (2001) supra). In the case of a specific interaction, only the fraction of the modified oligosaccharide with the right sequences can interact with the binding partner. Therefore, the fact that only a fraction of a modified oligosaccharide can bind to a binding partner indicates that the interaction is sequence specific. Using GMSA, the presence of sequence specific oligosaccharide-binding partner interactions can be determined.

Figure 4A:
FIG. 4A shows the results of a binding assay of an 18-mer oligosaccharide modified with 3-OST-1 and shifted with increasing amounts of AT-III.
Figure 4A:
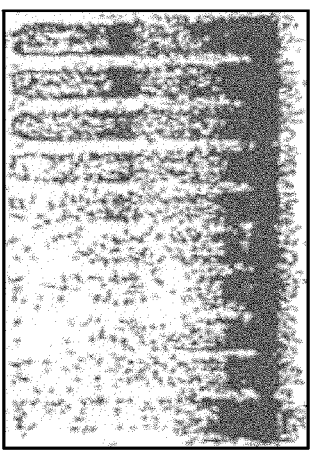
Figure 4C:
FIG. 4C shows the results of a binding assay of an 18-mer oligosaccharide modified with 3-OST-1 and 6-OST-1 and shifted with increasing amounts of AT-III.
Figure 4C:
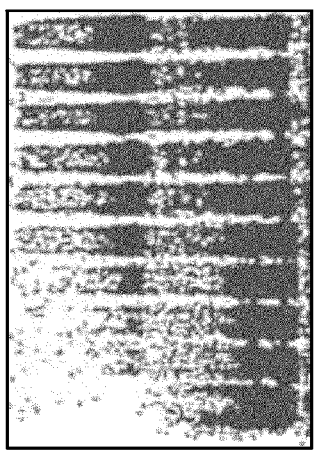

An octadecamer was radiolabeled with 3-OST-1 and/or 6-OST-1 as described above in Example 1, and the modified octadecamers were subject to GMSA. The gel was then analyzed by densitometry as described above in Example 1. FIG. 4A shows the results of a GMSA of 3-OST-1 treated octadecamer (i.e., 3-O sulfated). FIG. 4B shows the results of a GMSA of 6-OST-1 treated octadecamer (i.e., 6-O sulfated). FIG. 4A shows the results of a GMSA of 3-OST-1 and 6-OST-1 treated octadecamer (i.e., 3-O and 6-O sulfated). In each case, the amount of octadecamer that was bound to AT-III (i.e., the upper shifted band) increased with the amount of AT-III present in the binding reaction. This increase for each case approached a plateau value (FIG. 4D). For the 6-OST-I modification, about 25% of the octadecamer could bind to AT-III; for 3-OST-1 modification, about 40% of the octadecamer could bind to AT-III; and for the 3-OST-1 and 6-OST-1 double modification, about 50% of the octadecamer could bind to AT-III (FIG. 4D). The small additional increases at high levels of AT-III were likely caused by non-specific binding. This experiment demonstrated that the interactions between sulfated oligosaccharides, such as HS, and proteins, such as AT-III, are sequence specific.

Example 5

In vitro Reconstitution of AT-III Binding Sites

AT-III binding sites were reconstituted on completely desulfated and N-resulfated heparan sulfate (DSNS) by the addition of 3-O and 6-O sulfates to the oligosaccharide chain.

FIG. 5A shows the reconstitution of AT-III binding sites on DSNS. DSNS was modified with one or more of the sulfotransferases 2-OST, 3-OST-1, and 6-OST-1, as described in Experiment 1. Although the incorporation rates of [$^{35}$S]PAPS were different from enzyme to enzyme, roughly the same amounts of radioactivity (20,000 cpm) were used in the binding assay. When the DSNS chain was modified by 6-OST-1 alone, the chain did not bind to AT-Ill. Only a very slight amount of the 2-OST labeled DSNS chain could bind to AT-III. The 3-OST-1 labeled chain bound well to AT-III. When the DSNS chain was modified by both 6-OST-1 and 3-OST-1, the chain could strongly bind to AT-III; further addition of 2-OST did not change the binding significantly (FIG. 5A). The $K_d$ between the 3-OST-1 and 6-OST-1-modified DSNS and AT-III was calculated to be 0.24±0.07 μM, indicating that 3-OST-1 and 6-OST-1 were almost sufficient to generate AT-III binding sites on DSNS.

Since there are multiple isoforms for 3-O and 6-O sulfotransferases, we examined whether those isoforms could substitute for 3-OST-1 or 6-OST-1, respectively, in generating AT-III binding sites. FIG. 5B shows the reconstitution of AT-III binding sites on DSNS using one or more of the sulfotransferases 3-OST-1, 3-OST-2, 3-OST-3A, 3-OST-4, 6-OST-1, 6-OST-2A, 6-OST-2B, or 6-OST-3. The results showed that 3-OST-2, 3-OST-3A and 3-OST-4 could not substitute for 3-OST-1 in making the AT-III binding site, but 6-OST-2A, 6-OST-2B and 6-OST-3 could substitute for 6-OST-1 (FIG. 5B). These experiments demonstrated that 6-O sulfation can be carried out by different isoforms and that 3-O sulfation by 3-OST-1 and 6-O sulfation are the critical modification steps in making AT-III binding sites (Liu et al. (1999) J. Biol. Chem. 274: 5185-5192). These data were also consistent with a somatic mutagenesis study that demonstrated that 6-OST-1 was a critical modification enzyme in CHO cells for making AT-III binding sites (Zhang et al. (2001b) J. Biol. Chem. 276:42311-21). In addition, this experiment demonstrated that it is possible to generate oligosaccharide libraries by generating desired lengths of an oligosaccharide of interest and modifying the oligosaccharide with one or more modifying enzymes, e.g., sulfotransferases. Further, this experiment demonstrate that protein binding sites on oligosaccharides can be reconstituted by in vitro modification.

Example 6

Gel Mobility Shift Assay with Oligosaccharides and Other Proteins

Figure 6A:
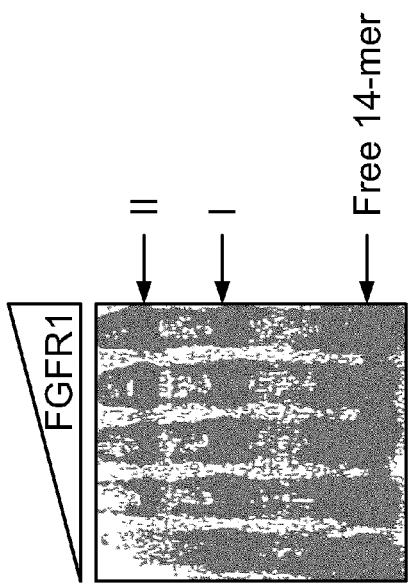
FIG. 6A shows the results of a binding assay for FGF and FGFR. A tetradecasaccharide was radiolabeled with 3-OST-1 and subject to GMSA with different proteins. In each reaction, 250 ng of protein and 20 ng of labeled oligosaccharide was used.
Figure 6B:
FIG. 6B shows the results of a GMSA demonstrating that FGF-HS can be supershifted by FGFR1. Each lane contained 50 ng of oligosaccharide, 250 ng of FGF1 and 0, 25, 50, 100, or 500 ng FGFR1, respectively, from left to right. Band I is a complex of FGF1-oligosaccharide. Band II is a complex of FGF1-FGFR1-oligosaccharide.

To demonstrate that the methods of the invention may be used to study the binding of any oligosaccharide to a binding partner, binding of an oligosaccharide to a number of proteins was examined. A tetradecamer oligosaccharide was radiolabeled with 3-OST-1 as described in Example 1 and incubated with 250 ng of various recombinant proteins, including AT-III, FGF1, FGF2, FGFR1, FGFR2, FGFR3, and FGFR4. With the exception of FGFR2, all recombinant proteins bound to the labeled oligosaccharide, as shown by shifted bands (FIG. 6A). The position of each shifted band varied from protein to protein, likely reflecting the differences in conformation, weight, and/or charge density of the oligosaccharide-protein complexes. FGF2 almost completely shifted the probe, suggesting that FGF2 may be least selective for the oligosaccharide (FIG. 6A). When both FGF1 and FGFR1 were applied to the binding assay, two bands appeared (FIG. 6B). The fast moving (i.e., lower) shifted band was an FGF1-oligosaccharide complex. The slow (i.e., upper) shifted band was likely a FGF1-FGFR1-oligosaccharide complex, since the fast moving band disappeared and the mass of slow band increased when more FGFR1 was added (FIG. 6B). This experiment demonstrated that in vitro modification and GMSA can be used as a general approach for studying oligosaccharide-protein interactions.

Example 7

Demonstration of HS:FGF1, HS:FGFR1 and a Ternary Complex Between FGF1, FGFR1 and HS Materials:
Heparin oligosaccharides (dp4 to dp24) were obtained from Iduron (Manchester, UK). FGF1 was obtained R&D Systems (Minneapolis, Minn.). Regular PAPS was obtained from Calbiochem (La Jolla, Calif.). 3-OST-1 and 6-OST-1 were prepared as previously described (Wu et al. (2002) supra). CHOpgsA-745 cell line and 6-O-desulfated heparin (6ODS) were obtained from the University of California, San Diego. Preparation of [$^{35}$S] labeled 3'-phosphoadenosine 5'-phosphosulfate ([35S]PAPS), radiolabeling of oligosaccharide and heparin, gel mobility shift assay, autoradiograph and gel analysis were described previously (Wu et al. (2002) supra). Anti-FGF1 antibody was obtained from Santa Cruz Biotechnology (Santa Cruz, Calif.). CHO-K1 cell line was obtained from ATCC (Manassas, Va.). Fetal bovine serum (FBS) was obtained from Life Technologies (Rockville, Md.). Protein A, Alexa Fluor® 647 conjugate was obtained from Molecular Probe (Eugene, Oreg.).

Human 6-OST-1 recombinant baculovirus was prepared using the pFastBas HT donor plasmid modified by the insertion of honeybee mellitin signal peptide (Liu et al. (1999) J. Biol. Chem. 274: 38155-38162) and the Bac-to-Bac baculovirus expression system (Life Technologies, Inc.) according to the manufacturer's protocol, except that recombinant bacmid DNA was purified using an endotoxin-free plasmid purification kit (Qiagen, Inc.) and transfection of Sf9 cells were scaled up to employ 3 μg of bacmid DNA and 6×10$^6$ exponentially growing cells in a 100-mm dish. At day 3 post-transfection, baculovirus was precipitated from the medium with 10% polyethylene glycol, 0.5 M NaCl at 12,000 g, re-suspended in 14 ml of medium, and applied to a 100-mm dish seeded with 1.5×10$^7$ Sf9 cells. Medium from the infected cells was harvested after 90 h of growth at 27° C., centrifuged at 400×g, made to 10 mM in Tris, adjusted to pH 8.0, and centrifuged at 4000×g. Clarified medium was diluted with an equal volume of cold 10 mM Tris-HCl, pH 8.0, and stirred for 30 min with 0.6 ml (packed volume) of Toyopearl 650M chromatographic media (TosoHaas). The heparin-Sepharose was packed into a column (0.4-4.75 cm), washed with 5 ml of TCG 50 (10 mM Tris-HCl, pH 8.0, 2% glycerol, 0.6% CHAPS, 50 mM NaCl), eluted with 1.2 ml of TCG 1000 (as above, but 1 M in NaCl) containing 10 mM imidazole, and concentrated to 0.25 ml in a Microcon YM-10 centrifugal filter (Millipore Corp.).

Histidine-tagged recombinant 6-OST-1 was affinity-purified by mixing the product eluted from heparin-Sepharose for 90 min at 4° C. with nickel-nitrilotriacetic acid magnetic agarose beads (Qiagen, Inc.) magnetically sedimented from 60 μl of suspension. The beads were washed twice with 0.125 ml of TCG 400 containing 20 mM imidazole and eluted twice with 0.03 ml of TCG 400 containing 250 mM imidazole. The combined elution fractions contained ~25% of the sulfotransferase activity present in the starting medium.

Bacterial expression and purification of 6-OST-1 was performed as follows. Expression vector pET15b was purchased from Novagen (Madison, Wis.). E. coli strains BL21 and DH5 were obtained through the ATCC (Manassas, Va.). An AseI restriction site was introduced at 211-216 bp, and a BamHI restriction site was introduced at 1344-1349 bp of human 6-OST-1 (Habuchi et al. (1998) J. Biol. Chem. 273: 9208-9213) (by PCR. The 6-OST-1 gene was then ligated into NdeI- and BamHI-digested pET15b and transformed into competent E. coli strain DH5. A BL21 colony containing 6-OST-1 in pET15b with confirmed sequence was used to inoculate 2 liters of LB containing 100 μg/ml ampicillin. The cultures were shaken in flasks at 250 rpm at 37° C. When the optical density at 600 nm reached 1.2, 1 mM isopropyl-1-thio-D-galactopyranoside was added to the cultures. The cultures were then agitated at 250 rpm overnight at room temperature. The cells were pelleted at 5000 rpm for 15 minutes. The supernatant was discarded, and the cell pellet was resuspended in 40 ml of 20 mM Tris, 500 mM NaCl, 0.6% CHAPS, 1% glycerol, and 5 mM imidazole, pH 7.9 ("binding buffer"). The cells were homogenized, and the homogenate was centrifuged at 13,000 rpm for 20 min. The supernatant was filtered through 0.2-μm filter paper and loaded onto a BioCAD HPLC system (PerSeptive Biosystems, Cambridge, Mass.) and purified using Ni2+ chelate chromatography. Briefly, the supernatant was loaded onto the column and washed with binding buffer until unbound material was washed off the column. Then, low affinity material was washed off the column using 20 mM Tris, 500 mM NaCl, 0.6% CHAPS, 1% glycerol, and 55 mM imidazole, pH 7.9, and 6-OST-1 was eluted from the column with 20 mM Tris, 500 mM NaCl, 0.6% CHAPS, 1% glycerol, and 500 mM imidazole, pH 7.9. The purity of the recombinant 6-OST-1 was determined using a silver-stained protein gel.

Figure 8:
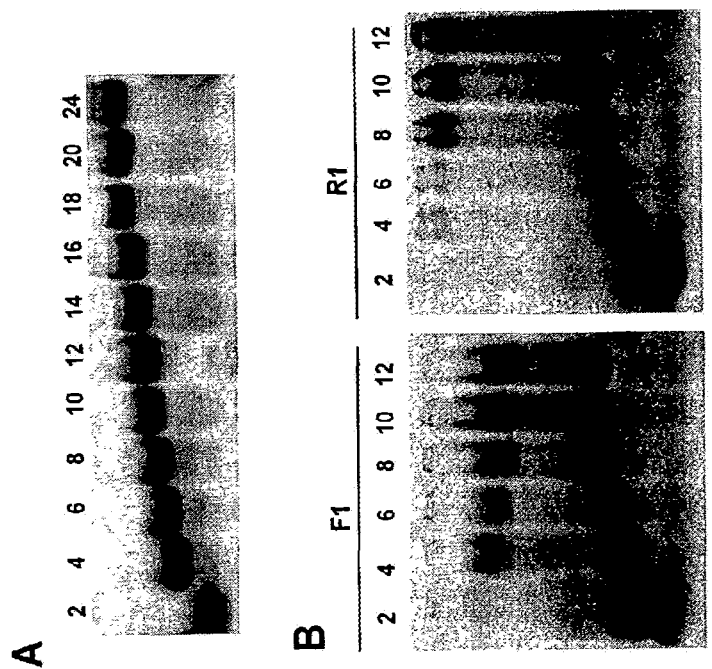
FIG. 8A shows an oligosaccharide ladder radiolabeled with 6-OST-1. The labeled ladder was separated by 15% PAGE. The disaccharide was obtained from enzyme digested radiolabeled heparin.
FIG. 8B shows an oligosaccharide labeling and shift assay with FGF1 and FGFR1. A GMSA was performed with FGF1 or FGFR1 and the labeled ladder of FIG. 8A.

A ladder of defined lengths of HS oligosaccharides was radiolabeled with 6-OST-1 (Wu et al. (2002) FASEB J. 16: 539-45). The labeled products were examined on a 15% PAGE gel (FIG. 8A). Disaccharide could not be labeled efficiently by 6-OST-1, therefore, the 6-O labeled disaccharide was prepared by digestion of the 6-O labeled tetradecasaccharide with a mixture of heparitinase I, heparitinase II, and heparinase. Briefly, the heparin sample (20 μg) was digested with a mixture of heparitinase I, heparitinase II, and heparinase (Seikagaku Corporation, Tokyo, Japan) at 37° C. for 2 hours in 50 μl buffer of 2 mM Ca(Ac)$_2$, 20 mM Na Ac, pH 7.0. The digestion products were separated with a C18-reversed phase column (IPRP-HPLC) (Vydac, Lake Forest, Calif.). The sample was eluted with 2.5%, 6%, 10.5%, 18%, 50% acetonitrile in 40 mM NH$_4$H$_2$PO$_4$ and 1 mM tetrabutylammonium dihydrophosphate (Sigma) for 15, 15, 45, 25, 20 minutes, respectively, and was monitored with light absorbance at 232 nm.

FGFR1 was prepared using standard molecular cloning techniques. Briefly, the extracellular domain of FGFR1, including Ig-like domain II and III (from residue 142 to 365) (Pellegrini et al. (2000) supra; Plotnikov et al. (1999) supra) was PCR cloned from a Human Placenta Quik-Clone™ cDNA library (Clontech, Palo Alto, Calif.). The PCR forward primer was GATAACACCAAACCAAACCG (SEQ ID NO:1) and the backward primer was CCTCTCTTC-CAGGGCTTCCA (SEQ ID NO:2). The PCR product was expressed in a pBAD/TOPO ThioFusion™ Expression System (Invitrogen, Carsbad, Calif.). The expressed protein was a fusion protein with thioredoxin at the C terminal and was refolded in 150 mM NaCl, 10 mM Tris pH 8.0, 10% glycerol, 1 mM L-Cystein.

The labeled ladder shown in FIG. 8A was subjected to a gel mobility shift assay with FGF1 and FGFR1 (FIG. 8B). FGF1 could bind to tetrasaccharide and longer chains, while FGFR1 only showed significant binding to octasaccharide and longer chains. The mobility of binary complex FGF1:HS was greater than that of FGFR1:HS. The bands shifted by FGF1 and FGFR1 exhibited a similar degree of tailing, which may have been caused by dissociation of the oligosaccharides from the respective binary complexes during electrophoresis. This indicated that FGF1 and FGFR1 have similar binding affinities to those oligosaccharides, which was consistent with previous reports (Mach et al. (1993) Biochemistry 32: 5480-5489; Powell et al. (2002) J. Biol. Chem. 277: 28554-28563; Wang et al. (1995) J. Biol. Chem. 270: 10231-10235).

To see if FGF1, FGFR1 and HS could form a ternary complex, equal amounts of FGF1 and FGFR1 were mixed with excess dodecasaccharide and subjected to a GMSA. A distinct band, with mobility greater than FGFR1:HS but less than FGF1:HS binary complexes, was observed (FIG. 9A), demonstrating the formation of the ternary complex between FGF1, FGFR1 and HS. The bands of the ternary complex were sharper than those of the binary complexes, suggesting tighter binding of HS in the ternary complex than in the binary complexes.

Figure 9B:
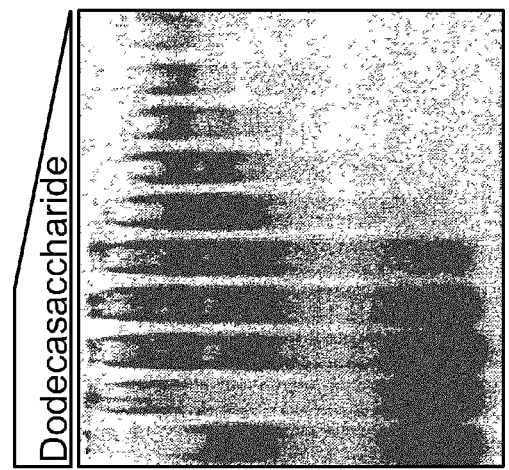
FIG. 9B shows FGF1:HS:FGFR1 ternary complex formation and the strong affinity of HS in the complex. HS had the strongest binding affinity in the ternary complex. From lane 3 to 10, constant molar equivalents of FGF1 and FGFR1, but decreasing amount of dodecasaccharide were applied. FGF1 only was in lane 1 and FGFR1 only was in lane 2.
Figure 9A:
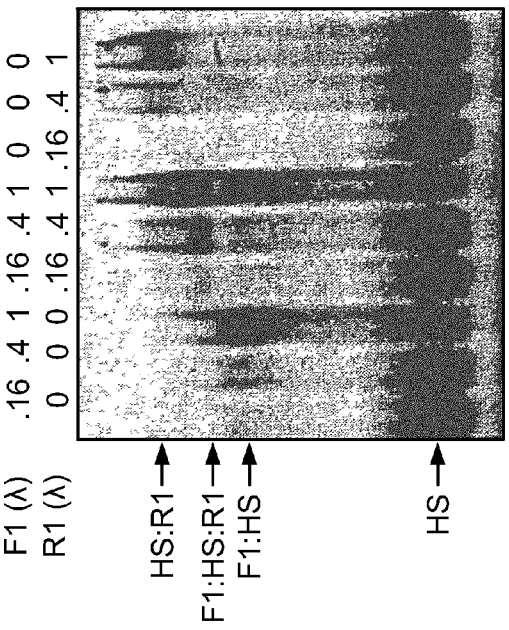
FIG. 9A shows FGF1:HS:FGFR1 ternary complex formation and the strong affinity of HS in the complex. The ternary complex moved distinctively in the native gel. The HS was a dodecamer labeled with 3-OST-1.

To confirm that HS had higher affinity to FGF1 and FGFR1 in the ternary complex, equal amounts of FGF1 and FGFR1 and different amounts of oligosaccharide were subjected to a gel mobility shift assay (FIG. 9B). As the amount of oligosaccharide in the reaction decreased, FGFR1:HS disappeared first followed by the disappearance of FGF1:HS, until only the ternary complex FGFR1:HS:FGF1 remained. These data demonstrate that HS has the highest affinity in the ternary complex.

Figure 9C:
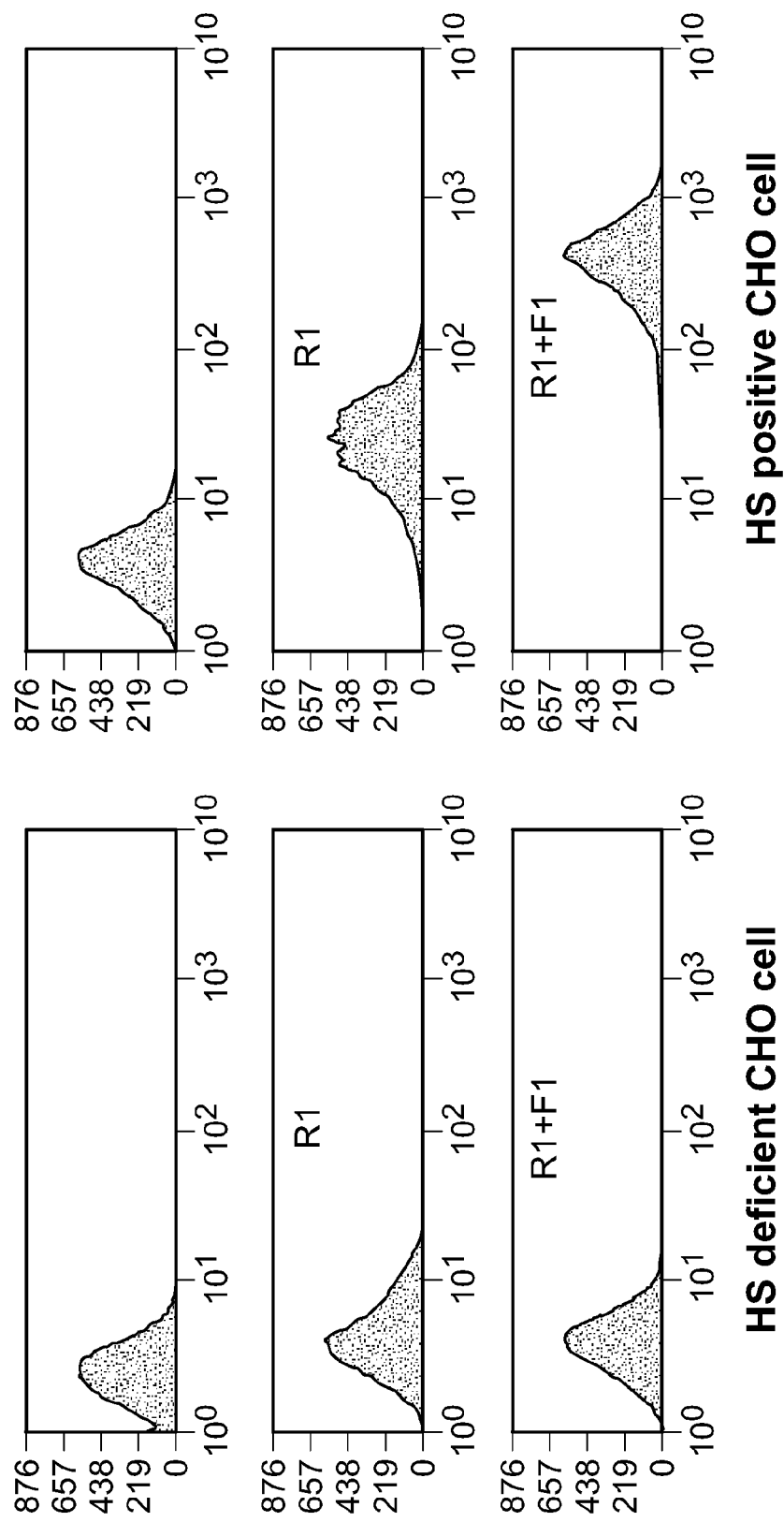
FIG. 9C shows FGF1:HS:FGFR1 ternary complex formation and the strong affinity of HS in the complex. The cell surface HS showed much stronger affinity to FGFR1 in the presence of FGF1 in flow cytometry assays. Left panel, HS-expressing CHO K1 cell. Right panel, HS-deficient CHOpgsA-745 cell. The fluorescence tagged FGFR1 was monitored.
Figure 10:
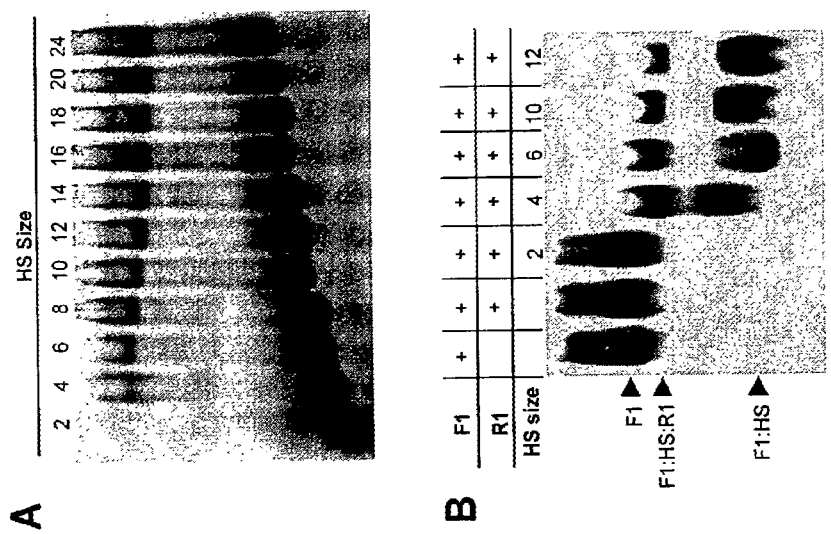
FIG. 10A shows the measurement of the minimal oligosaccharide in the ternary complex of FGF1:HS:FGFR1. The minimal oligosaccharide was measured to be a tetramer. Each lane contained 250 ng of radiolabeled oligosaccharide, 16 pmol of FGF1 and 64 pmol of FGFR1.
FIG. 10B shows the measurement of the minimal oligosaccharide in the ternary complex of FGF1:HS:FGFR1. The gel shift assay was visualized with anti-FGF1. In order to visualize the binary complex and ternary complex, excess amount of cold oligosaccharide and limited amount of FGFR1 were applied to each lane.

This observation was also confirmed in flow cytometry assays, where the binding of cell surface HS to fluorescent tagged FGFR1 was monitored (FIG. 9C). Briefly, nearly confluent monolayers of cells in a T-75 flask were detached by adding 10 ml phosphate buffered saline (PBS) containing 10% FBS and 2 mM EDTA and centrifuged. The cell pellets were placed on ice. About $1 \times 10^6$ cells were first mixed with 20 µl PBS containing 10% FBS and 1 µg FGFR1β/Fc, then 4 µg of protein A, Alexa Fluor® 647 conjugate was added. After 15 minutes of incubation, the cells were washed once with 1 ml of PBS and resuspended in 300 µl PBS containing 10% FBS. Flow cytometry was performed with FACScan and FACStar instruments (Becton Dickinson).

HS-expressing wild type CHO-K1 cells had weak affinity for FGFR1, but this binding was greatly enhanced in the presence of FGF1, as shown with the shift of the cell histogram. On the other hand, the HS-deficient CHOpgsA-745 cells showed no affinity to FGFR1, even in the presence of FGF1, which suggested that the binding was through HS. Similar results were obtained when the binding of the HS to fluorescent tagged FGF1 was monitored in flow cytometry assays (data not shown).

Example 8

The Minimal Oligosaccharide Length Supporting the Ternary Complex Formation

To determine this minimum length of oligosaccharide that can initiate the ternary complex with FGF1 and FGFR1 and cause activation of FGFR, the labeled ladder of FIG. 8A was used in a GMSA with both FGF1 and FGFR1 (FIG. 10A). Tetrasaccharide (dp4) and larger oligosaccharides, but not disaccharide, supported the formation of the ternary complex.

To confirm this observation, a GMSA was also visualized with anti-FGF1 antibody. FGF1 has a low mobility in a native gel electrophoresis, because it is not as negatively charged as HS. The binding of HS to FGF1 adds negative charges and increase the mobility of the protein. When FGF1 and FGFR1 were incubated with tetrasaccharide or longer oligosaccharides, two bands of increased mobility were observed (FIG. 10B), but this did not occur with disaccharide. The faster-moving band was the complex of FGF1:HS and the slower-moving band was the ternary complex of FGFR1:FGF1:HS. This experiment again demonstrated that tetrasaccharide is the minimal oligosaccharide required for the formation of a ternary complex among FGF1, FGFR1 and HS.

Although various models have been proposed for the formation of FGF signaling complex, the mechanism through which HS assists the formation of the complex is not clear. Generally, there are two modes of viewing HS/protein interaction. In the first mode, HS is viewed as a thread that links proteins in the fashion of beads on a string (cis mode); in the second mode, HS is regarded as a ribbon or a rod, and can bind to proteins with different sides or faces (trans mode). In the cis mode, one possibility is that there are both FGF and FGFR binding sites along HS, and simultaneous binding of FGFs and FGFRs will cause the formation of the signaling complex (Guimond et al. (1993) supra). Another possibility is that HS only binds FGFs, which in turn bind to receptors and cause the dimerization of FGFRs (Spivak-Kroizman et al. (1994) supra). The GMSAs provided herein demonstrated that the minimum FGF1-binding HS was a tetrasaccharide, which is consistent with result from protection assays (Mach et al. (1993) supra), and that the minimum FGFR1-binding HS was an octasaccharide. In theory, the length of two contiguous FGF1 binding sites on HS will span at least eight sugar residues, and the length needed for one FGF1 site and one FGFR1 site will cover at least twelve sugar residues. The cis mode can not explain the findings from the present and past studies that shorter oligosaccharides can initiate the ternary complex formation and activate FGF receptors (Delehedde et al. (2002) supra; Ornitz et al. (1995) supra); Ostrovsky et al. (2002) supra. It is also unlikely that FGFR1 does not interact with HS in the signaling complex. Because the binding affinity of HS to FGFR1 is similar to that to FGF1 (Mach et al. (1993) supra; Powell et al. (2002) supra), in a ternary complex without HS/FGFR1 interaction, FGFR1 competes with FGF1 for the HS and makes the complex thermodynamically unstable.

Not to be limited to any particular theory, the trans mode better describes the FGF1 signaling complex. In a trans mode, proteins bind to a single oligosaccharide from opposite sides; not depend, therefore, upon HS length. In a typical model of this kind (DiGabricle et al. (1998) supra), two FGFs bind to an oligosaccharide from the opposite sides, and the FGFs in turn bind to two FGFRs. However, there is no HS/FGFR interaction in this kind of model, which is unlikely, as stated previously. Also, the two receptors are physically separated, which would make it difficult for them to trans-phosphorylate each other.

Example 9

The Stoichiometry of the Ternary Complex

Figure 11:
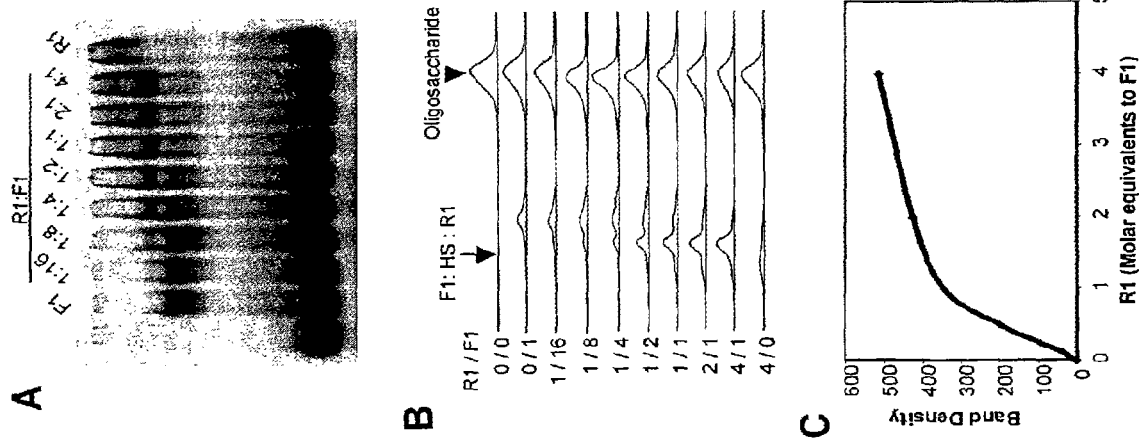
FIG. 11A shows the measurement of the molar ratio between FGF1 and FGFR1 in the ternary complex. The GMSA contained the same amount of radiolabeled dodecasaccharide and FGF1, but an increasing amount of FGFR1. From lane 2 to 10, 0, 1/16, 1/8, 1/4, 1/2, 1, 2, 4, or 4 molar equivalents of FGFR1 were applied.
FIG. 11B shows a densitometry analysis of the data shown in FIG. 11A.
FIG. 11C shows the band intensity of the ternary complex of FIG. 11B was plotted with the molar equivalents of FGFR1 to FGF1.

Knowing the stoichiometry of the formed complex is essential for understanding how the signaling pathway is triggered. The idea of that FGF receptors are dimerized upon activation is generally accepted, but there are still disagreements in the literature on the stoichiometry of FGF and HS in the signaling complex, and the relationship between the stoichiometry and the size of the HS is not clear. The ratio of FGF1 and FGFR1 in the ternary complex was determined by mixing a fixed amount of FGF1 with increasing of FGFR1 in binding reactions (FIG. 11A). With the increase of FGFR1, the intensity of the bands of the ternary complex also increased. The bands were then subjected to densitometry analysis and plotted against the molar equivalents of FGFR1 (FIGS. 11B and 11C). The slope of the curve declined sharply where the amount of FGFR1 is equal to FGF1 (FIG. 11C). This indicated that FGF1 and FGFR1 have a 1:1 ratio in the ternary complex. The continuing increase in band intensity above equivalence may have been caused by a shift of equilibrium, as excess FGFR1 drove more ternary complex to formation and caused the disappearance of the FGF1:HS binary complex. At the level of 4 equivalents of FGFR1, there was almost no FGF1:HS complex observed.

The stoichiometry of oligosaccharide in the ternary complex was also determined by densitometry analysis. In FIG. 10A, each lane contained 250 ng of oligosaccharide and 16 pmol of FGF1 and 64 pmol of FGFR1. The amount of the shifted oligosaccharide from lane 2 to lane 11 was then calculated by densitometry analysis, and the molar ratios between the oligosaccharides and FGF1 were determined (Table 1). The ratio was consistently near 1:1, independent of the size of HS. Considering the 1:1 ratio between FGF1 and FGFR1, this result suggested that the components of the ternary complex have a molar ratio of 1:1:1 of FGF1:FGFR1: oligosaccharide.

TABLE 2

The molar ratio of oligosaccharides (oligo) to FGF1 in the ternary complex[1]

| size | Complex density | Total density | % | Shifted oligo (ng) | MW[2] | Shifted oligo(pmol) | Olio-/FGF1 |
|---|---|---|---|---|---|---|---|
| 4 | 207 | 2675 | 7.73 | 19.3 | 1154 | 16.7 | 1.04 |
| 6 | 229 | 2636 | 8.68 | 21.7 | 1731 | 12.5 | 0.78 |
| 8 | 393 | 2921 | 13.5 | 33.6 | 2308 | 14.6 | 0.90 |
| 10 | 704 | 3671 | 19.2 | 47.9 | 2885 | 16.6 | 1.03 |
| 12 | 739 | 3437 | 21.5 | 53.8 | 3462 | 15.5 | 0.96 |
| 14 | 827 | 3349 | 24.7 | 61.7 | 4039 | 15.2 | 0.95 |
| 16 | 1240 | 3441 | 36.0 | 90.0 | 4616 | 19.5 | 1.21 |
| 18 | 1020 | 3473 | 29.4 | 73.4 | 5193 | 14.1 | 0.88 |
| 20 | 1269 | 3812 | 33.3 | 83.2 | 5770 | 14.4 | 0.90 |
| 24 | 1463 | 3833 | 38.2 | 95.4 | 6924 | 13.8 | 0.86 |

[1]Each binding reaction contained 16.1 pmol of FGF1, 64 pmol of FGFR1 and 250 ng of oligosaccharide.
[2]Molecular weight. It was calculated based on the MW of fully sulfated disaccharide, which is 577.

Example 10

Requirement of Specific Modification in HS for the Ternary Complex Formation

Figure 12:
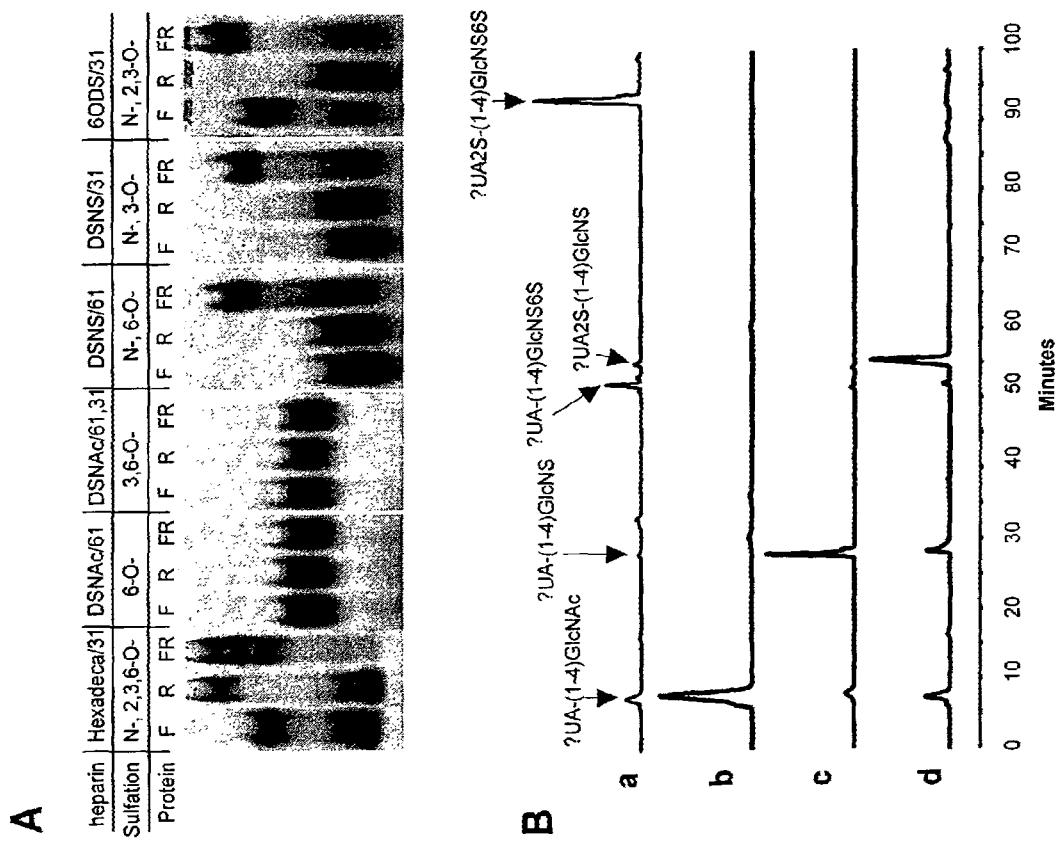
FIG. 12A shows that critical sulfate groups on HS are involved in the formation of the ternary complex. Wild type heparin oligosaccharide and modified heparin were radiolabeled with 3-OST-1 and/or 6-OST-1 and shifted with FGF1/ or FGFR1. Hexadeca/31, heparin hexadecasaccharide labeled with 3-OST-1; DSNAc/61, DSNAc labeled with 6-OST-1; DSNAc/31,61, DSNAc labeled with both 3-OST-1 and 6-OST-1; DSNS/61, DSNS labeled with 6-OST-1; DSNS/31, DSNS labeled with 3-OST-1; 6ODS/31, 6ODS labeled with 3-OST-1; F, FGF1; R, FGFR1; FR, FGF1 and FGFR1.
FIG. 12B shows that critical sulfate groups on HS are involved in the formation of the ternary complex. Disaccharide analysis of the heparin and chemically modified heparins. a, wild type heparin; b, DSNAc; c, DSNS; and d, 6ODS.

Because different critical sulfate groups are involved in FGF/HS interactions (Guimond et al. (1993) supra; Kreuger et al. (2001) J. Biol. Chem. 276: 30744-30752; Pye et al. (2000) supra) and FGFR/HS interactions (McKeehan et al. (1999) supra; Pantoliano et al. (1994) Biochemistry 33: 10229-10248; Pye et al. (1998) supra), HS is usually considered as a bridge, with one region interacting with FGF and another region interacting with FGFR (Guimond et al. (1993) supra). To determine whether the sulfate groups are additively important in the ternary complex formation, completely desulfated, N-acetylated (DSNAc), completely desulfated, N-resulfated (DSNS) and 6-O desulfated (6ODS) heparin (Seikagaku America, Falmouth, Mass.) were used as starting material to investigate the role of critical groups (FIG. 12A). When DSNAc was modified with 6-OST-1, or 6-OST-1 plus 3-OST-1, it could not bind to either FGF1 or FGFR1 and failed to form the ternary complex with FGF1 and FGFR1. When DSNS was modified with 6-OST-1 or 3-OST-1, it still could not bind to either FGF1 or FGFR1 individually, but could initiate the ternary complex formation. When 6ODS was modified with 3-OST-1, it could not bind to FGFR1, but could bind to FGF1 and initiate the ternary complex formation. These experiments demonstrated that N-sulfation and perhaps some O-sulfation are critical for the ternary complex formation. On the contrary, 6-O sulfation, which was thought to be critical for FGFR1 binding (McKeehan et al. (1999) supra; Pye et al. (1998) supra) is not critical for the ternary complex formation.

To validate the results for chemically modified heparin, disaccharide analysis of these compounds was performed (FIG. 12B). The major disaccharides found in DSNAc and DSNS were ΔUA-(1-4)GlcNAc and ΔUA-(1-4)GlcNS, respectively. Only very small amounts of ΔUA2S-(1-4) GlcNS and ΔUA-(1-4)GlcNS6S were observed in DSNS, which might be due to non-specific sulfation during the chemical N-sulfation step. The major disaccharide found in 6ODS was ΔUA2S-(1-4)GlcNS, as a result of the 6-O desulfation of the trisulfated disaccharide, ΔUA2S-(1-4) GlcNS6S. The trisulfated disaccharide was not found in any of the three chemically modified heparins, suggesting that it may not be critical for the ternary complex formation. Because of the presence of a small amount of ΔUA2S-(1-4) GlcNS in DSNS, and ΔUA-(1-4)GlcNS6S in 6ODS, it is hard to reach a definitive conclusion as to the importance of 2-O and 6-O sulfations in the ternary complex formation; nevertheless, since 2-O and 6-O sulfations in DSNS and 6ODS, respectively, were significantly lower than those in the wild type heparin, 2-O and 6-O sulfations may not be as important in the ternary complex formation as in the binary complex formation.

Example 11

Figure 13:
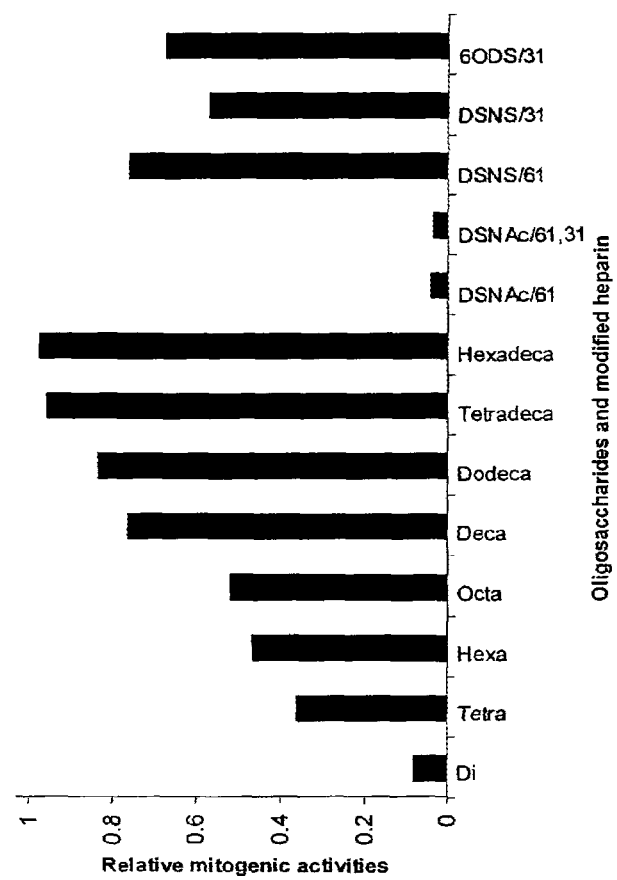
FIG. 13 shows a biological assay of heparin oligosaccharides and chemically modified heparins in a FGFR1 expressing BaF3 cell line with FGF1 as ligand. The names of the sample were specified in FIG. 12. The activities were normalized with that of wild heparin.

The FGF1:HS:FGFR1 Complex Formation is a Prerequisite for FGF1 Stimulated Cell Growth Although ternary complex formation was observed by GMSA with various modified heparins and heparin oligosaccharides, it was important to know if the formed ternary complexes are biologically relevant. The oligosaccharides and modified heparins were tested for their mitogenic activities in an FGFR1-expressing BaF cell system (Ornitz et al. (1995) supra) stimulated with FGF1 (FIG. 13). Briefly, suspension cultures of FGFR1 expressing BaF3 cells were maintained in AIM V media (Gibco BRL, Rockville, Mass.), supplemented with 5 nM recombinant mouse IL-3 (R & D Systems). For mitogenic assays, 50 µl of AIM V media (serum free) containing HSs and FGF-1 at final concentrations of 1 µg/ml and 5 nM respectively, were plated into a 96 well assay plate. Cells were washed and resuspended in AIM V media (serum free) and 2,500 cells were added to each well for a total volume of 100 µl. The cells were then incubated at 37° C. with 5% $CO_2$ for 24 hours. 100 µl Syto-11 dye (Molecular Probes, Eugene, Oreg.), which was prepared in 10 mM Tris, 1 mM EDTA, 50 mM NaCl, pH 8.0, was added to each well and incubated for 30 minutes at 37° C. The sample was excited at 508 nm and the fluorescence emission at 527 nm was then measured using the SpectraMax Gemini XS (Molecular Devices, Sunnyvale, Calif.). The data was analyzed with Softmax software and each data point presented was the average of a triplicate determination.

Disaccharide exhibited background mitogenic activity; tetramer, hexamer and octamer oligosaccharides exhibited medium mitogenic activities; and decasaccharide and longer oligosaccharides exhibited mitogenic activities comparable to that of heparin. The 6-O and 3-O sulfated DSNAc, which didn't support the ternary complex formation, exhibited almost no activity, but 6-O or 3-O sulfated DSNS and 3-O sulfated 6ODS, which supported ternary complex formation, showed significant activities. Thus the abilities of these oligosaccharides and modified heparins to initiate FGF1:HS:FGFR1 ternary complex (FIGS. 10A, 12B) correlated well with their mitogenic activities (FIG. 13). The observed ternary complexes were therefore active biological complexes and their formation is a prerequisite for FGFR1 activation.

Previously, it was widely accepted that a single oligosaccharide links both FGF and FGFR to form an FGF signaling complex. Schlessinger's "two-end" model (Schlessinger et al. (2000) supra) based on soaking oligosaccharide with preformed FGF2:FGFR1 crystal (Plotnikov et al. (1999) supra) provided an alternative model. In this new model, two antiparallel oligosaccharides are incorporated and the oligosaccharide can be as short as hexasaccharide. The complex is a dimer consisting of two 1:1:1 FGF:HS:FGFR half complexes and is stabilized via both FGFR/FGFR and HS/FGFR contacts. Within each 1:1:1 FGF:HS:FGFR complex, the hexasaccharide not only makes numerous contacts with both FGF and FGFR, thereby augmenting FGF/FGFR binding, but also makes contacts with FGFR1 in the neighboring half complex, thus playing a dual role in the ternary complex formation. Recently, this model has been supported by biological activity studies (Zhang et al. (2001) supra), where soluble HS proteoglycans, obtained by trypsinization from cells or by immuno-purification from cell extracts, did not promote FGF2-induced FGFR1-phosphorylation, yet a further treatment with heparitinase converted these proteoglycans into potent activators of FGF2/FGFR1 signaling. The methods of the invention have demonstrated that shorter oligosaccharides can initiate ternary complex formation and activate receptors, but also demonstrate that the HS has 1:1 stoichiometry with FGF1. Moreover, the 1:1 ratio between HS and FGF1 was found not only with hexasaccharide, but also with longer oligosaccharides up to dp24.

Although hexasaccharide was the smallest oligosaccharide shown to be effective in Schlessinger's model (Schlessinger et al. (2000) supra), the methods of the invention demonstrated that a tetrasaccharide can still make effective contacts with FGF1 and FGFR1 in the ternary complex. According to Schlessinger's crystal structure (Schlessinger et al. (2000) supra), only the first six sugar residues at the non-reducing end of a decasaccharide make 30 hydrogen bonds, including 9 with FGFR, 16 with FGF in the same half complex, and 5 with FGFR in the adjoining half complex. Among these, all the contacts to the FGFR, and 8 out of the 16 contacts to the FGF come from the first four sugar residues. On the other hand, the first two sugar residues only make 12 contacts, with only one to FGF, while the next two sugar residues make 10 contacts, with none to the FGFR in the same half complex. This suggests that a tetrasaccharide, but not a disaccharide, can fulfill the dual role played by a hexasaccharide in the ternary complex formation, and thus explains why a tetrasaccharide was the minimum oligosaccharide capable of initiating the ternary complex formation and possessing biological activity. Recently, tetrasaccharide has also been reported to bind FGF2 and promote cell growth (Delehedde et al. (2002) supra; Ostrovsky et al. (2002) supra; Zhou et al. (1997) supra).

Shorter oligosaccharides (dp4, dp 6, dp8) showed lower mitogenic activity than longer oligosaccharides (FIG. 13), even though a tetrasaccharide or hexasaccharide is sufficient for the formation of the molecular signaling complex. Not to be limited to any particular theory, one explanation is that adjacent HS sequences participate in the recruitment of FGF1 or FGFR1 to form the ternary complex. The probability of an FGF1, an HS, and an FGFR1 to bind each other simultaneously on a cell surface, is probably low. It is more likely that HS first associates with one of the proteins, FGFR1 for example, and then the unbound region of HS functions as a recruiter, where one FGF1 can bind and join the complex by proximity.

Shorter oligosaccharides (tetra- and hexasaccharide) did not bind FGFR1 significantly (FIG. 8B) although they could initiate signaling complex formation and have biological activity. 6-O or 3-O modified DSNS that did not bind either FGF1 or FGFR1, could still initiate the signaling complex (FIG. 12A) and have biological activity (FIG. 13). For those HSs that did bind to FGF1 and FGFR1 individually, the affinity in the ternary complex was much higher than in the binary complexes (FIGS. 9B, 9C). These results indicate that the mechanism for HS binding to FGF1:FGFR1 binary complex is different from that to individual FGF1 or FGFR1. One explanation of this is that the binding between FGF1 and FGFR1 creates a novel HS binding site, which was shown in Plotnikov and Schlessinger's crystal structures (Plotnikov et al. (1999) supra; Schlessinger et al. (2000) supra), and that the HS-binding affinity of this new site is higher than that of the sites on FGF1 or FGFR1. It is possible that, in the new binding site, the contacts could be made through different functional groups on HS.

To confirm the above assumptions, the functional groups on HS in the FGF1:HS:FGFR1 ternary complex were examined. N- and perhaps some O-sulfation on HS were critical for the ternary complex formation, and these groups are not the simple additive combination of the groups on HS critical for FGF1:HS and FGFR1:HS binary complexes. Previously, both 2-O and 6-O sulfations were shown to be critical for FGF1 (Guimond et al. (1993) supra; Ishihara et al. (2000) J. Biol. Chem. 275: 25949-58) and FGFR1 binding (Lundin et al. (2000) supra). Although 6-O desulfated heparin did not bind to FGFR1 in our experiment, it still could initiate a ternary complex and had mitogenic activity, which is consistent with, and explains, the previous report that 6-O desulfated heparin showed mitogenic activity (Kariya et al. (2002) J. Am. Chem. Soc. 124: 8707-8718).

Figure 14:
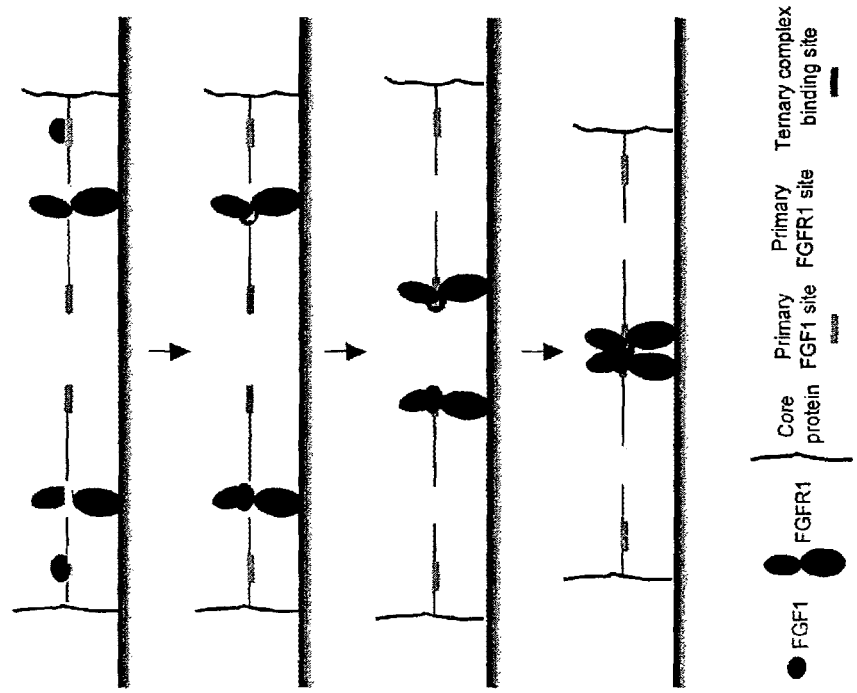
FIG. 14 shows a proposed 2:2:2 dimerization mechanism of FGFR1. FGF1 and FGFR1 have their primary binding sites inside the heparan sulfate chain. Half complexes form along the HS chains and then move to the none-reducing ends of the heparan sulfate, where two half complexes associate to form an active molecular signaling complex.

The fact that different binding mechanisms and different critical functional groups on HS are involved in the ternary complex formation indicates that the ternary complex may form on a distinct site on HS. For all tested oligosaccharides, the 1:1:1 ratio among FGF1, HS and FGFR1 (Table 1) implies that there is only one site where the ternary complex can form on each HS. According to Schlessinger's model, this site is always at the non-reducing end of HS. On the other hand, there could be multiple internal binding sites along the HS chain for FGF1 (Mach et al. (1993) supra) and FGFR1. Binding of FGF1 and FGFR1 to these sites probably constitutes a recruiting mechanism and facilitates the association of FGF1 and FGFR1 at the non-reducing end for the formation of the ternary complex (FIG. 14). Shorter oligosaccharides (tetra-, hexa-, and octasaccharide) lacking these FGF1 and FGFR1 do not form a ternary complex and thus explain why they showed less biological activities (FIG. 13). On the other hand, decasaccharides and longer oligosaccharides might have one or more of these binding sites, thus showed higher mitogenic activities (FIG. 13).

Overall, a direct link among critical groups on HS, FGF1 signaling complex formation, and cell growth was examined. The regulatory role of HS in organ development and cell proliferation has been observed before (Allen et al. (2001) supra; Brickman et al. (1998) J. Biol. Chem. 273: 4350-4359; Lindahl et al. (1998) supra), but the mechanism of this regulation was obscure. It is possible that a cell could regulate its own growth, through altering the critical groups on HS thus affecting the formation of specific FGF signaling complexes. The observation of critical groups on HS for FGF signaling complex strongly support the idea that HS is a regulatory element in the FGF signaling pathway.

Modification of HS with critical groups likely results from the operation of a set of tightly regulated modification enzymes. Recently, the gene structures for almost all of these enzymes have been elucidated, and it has been shown that N, 3-O and 6-O sulfotransferases exhibit genetic polymorphism and encode distinct isoforms (Esko and Selleck (2002) supra). These isoforms differ in substrate specificity and expression pattern, both spatially and temporally (Esko and Selleck (2002) supra), which may cause the specific modification on HS. Further study of these enzymes is crucial to our understanding of specific modifications on HS.

In an embodiment, the ternary complex—supporting heparin is reconstituted with these modification enzymes, because DSNAc has the basic structure of heparin yet lacks all sulfation. The critical sulfate groups as well as the critical modification enzymes may then be determined. For example, a novel assay for HS with coupled ion pair-reverse phase capillary high performance liquid chromatography and microelectrospray ionization time-of-flight mass spectrometry has been tested (Kuberan et al. (2002) supra). This new technique will allow for the determine of the distance between these critical groups.

Using chemically and enzymatically modified heparin sulfates and gel mobility shift assay, the formation of FGF1 signaling complex and study the physical parameters of HS in FGF signaling complex formation in a physiological condition without disturbing the natural structure or conformation of individual components was studied. The foregoing results concerning the minimal oligosaccharide, stoichiometry of HS, and the critical functional groups support a revised 2:2:2 FGF1:HS:FGFR1 signaling model (FIG. 14). The information about HS in AT-III binding and FGF ternary complex formation provides new insights for the design of heparin oligosaccharide mimetics that can specifically target individual growth factors involved in human diseases.

Equivalents

The invention may be embodied in other specific forms without departing from the spirit or essential characteristics thereof. The foregoing embodiments are therefore to be considered in all respects illustrative rather than limiting of the invention described herein.

The invention claimed is:

1. A method for detecting and characterizing binding between an isolated oligosaccharide and a binding partner, comprising the steps of:
 contacting an isolated oligosaccharide with a binding partner under conditions that allow binding of the oligosaccharide with the binding partner to form an oligosaccharide-binding partner complex;
 detecting the presence of the oligosaccharide-binding partner complex by subjecting the oligosaccharide-binding partner complex to a gel mobility shift assay having a native gel; and
 characterizing the binding partner that binds to the oligosaccharide in the oligosaccharide-binding partner complex,
 wherein the isolated oligosaccharide comprises heparan sulfate, chondroitin sulfate, dermatan sulfate, and/or keratan sulfate.

2. The method of claim 1, further comprising the step of modifying the oligosaccharide to contain at least one functional group.

3. The method of claim 1, wherein the oligosaccharide comprises between 4 and 300 saccharides.

4. The method of claim 1, wherein the oligosaccharide comprises at least a pentasaccharide.

5. The method of claim 1, wherein the oligosaccharide comprises heparan sulfate.

6. The method of claim 1, wherein the oligosaccharide is manufactured in vitro.

7. The method of claim 1, wherein the oligosaccharide is derived from an in vivo tissue sample.

8. The method of claim 1, wherein the oligosaccharide is modified in vitro.

9. The method of claim 1, wherein the oligosaccharide is modified in vitro with 3-OST-1 and/or 6-OST-1.

10. The method of claim 1, wherein the oligosaccharide is modified in vitro with at least one sulfotransferase selected from the group consisting of 2-OST, 3-OST-2, 3-OST-3A, 3-OST-4, 6OST-2A, 6-OST-2B, and 6-OST-3.

11. The method of claim 1, wherein the oligosaccharide is modified in vitro with an Ndeacetylase/N-sulfotransferase (NDST).

12. The method of claim 1, wherein the NDST is selected from the group consisting of NDSTI, NDST2, NDST3, and NDST4.

13. The method of claim 1, wherein the binding partner is a protein.

14. The method of claim 1, wherein the binding partner is selected from the group consisting of antithrombin III (AT-III), a fibroblast growth factor (FGF), fibroblast growth factor receptor (FGFR), vascular endothelial growth factor (VEGF), placental growth factor (PIGF), heparinbinding EGF- like growth factor, hepatocyte growth factor (HGF), transforming growth factorbeta (TGF-beta), platelet-derived growth factor (PDGF), pleiotrophin, platelet factor-4 (PF-4), interleukin-8 (IL-8), macrophage inflammatory protein-1 (MIP-1), interferon-g-inducible protein-10 (IP-10), interferon-gamma (IFN-gamma), and HIV-Tat transactivating factor.

15. The method of claim 1, wherein the binding partner is a peptide.

16. The method of claim 1, wherein the binding partner is an antibody.

17. The method of claim 1, wherein the binding partner comprises a detectable label.

18. The method of claim 1, wherein the oligosaccharide comprises a detectable label.

19. The method of claim 17 or 18, wherein the detectable label is a radioactive label.

20. The method of claim 17 or 18, wherein the detectable label is a non-radioactive label selected from the group consisting of biotin, fluorescein, and green fluorescent protein.

21. The method of claim 1, wherein the gel is selected from the group consisting of a vertical gel, a horizontal gel, and a capillary gel.

22. The method of claim 1, wherein the gel is subjected to autoradiography.

23. The method of claim 1, further comprising a step of calculating a dissociation constant for the oligosaccharide-binding partner complex using densitometry.

* * * * *